(12) United States Patent
Schecter

(10) Patent No.: US 8,956,304 B2
(45) Date of Patent: Feb. 17, 2015

(54) CARDIOVASCULAR HAPTIC HANDLE SYSTEM

(71) Applicant: Stuart O. Schecter, Great Neck, NY (US)

(72) Inventor: Stuart O. Schecter, Great Neck, NY (US)

(73) Assignee: Stuart Schecter LLC, Great Neck, NY (US)

( * ) Notice: Subject to any disclaimer, the term of this patent is extended or adjusted under 35 U.S.C. 154(b) by 0 days.

(21) Appl. No.: 14/105,749

(22) Filed: Dec. 13, 2013

(65) Prior Publication Data

US 2014/0207010 A1 Jul. 24, 2014

Related U.S. Application Data

(60) Continuation of application No. 13/448,879, filed on Apr. 17, 2012, now Pat. No. 8,663,122, which is a continuation of application No. 12/836,636, filed on Jul. 15, 2010, now abandoned, which is a (Continued)

(51) Int. Cl.
*A61B 5/02* (2006.01)
*A61B 5/11* (2006.01)
*A61B 5/00* (2006.01)
*A61B 5/029* (2006.01)
*A61B 8/08* (2006.01)

(52) U.S. Cl.
CPC .............. *A61B 5/1102* (2013.01); *A61B 5/0031* (2013.01); *A61B 5/029* (2013.01); *A61B 8/08* (2013.01)
USPC .......................................... 600/508; 600/512

(58) Field of Classification Search
USPC .......................................... 600/508, 512, 514
See application file for complete search history.

(56) References Cited

U.S. PATENT DOCUMENTS

| | | | |
|---|---|---|---|
| 3,184,842 | A | 5/1965 | Nicholas |
| 4,019,073 | A | 4/1977 | Vishnevsky et al. |

(Continued)

FOREIGN PATENT DOCUMENTS

| | | |
|---|---|---|
| EP | 0970663 | 1/2000 |
| KR | 20110004401 A | 1/2011 |

(Continued)

OTHER PUBLICATIONS

U.S. Appl. No. 60/647,102, filed Jan. 1, 2005.

(Continued)

*Primary Examiner* — Joseph Dietrich
(74) *Attorney, Agent, or Firm* — Patterson Thuente Pedersen, P.A.

(57) ABSTRACT

Cardiac tissue motion characteristics acquired by novel cardiac sensors are analyzed and processed for the derivation of physiological indices. The indices are output to a hand held local or remote volumetric haptic display and enable an operator to obtain motion related dynamic characteristics of cardiac tissues. The ability to tactually sense the motion of cardiac tissue and the affect on such motion from inserted cardiovascular instrumentation enhances the operator's performance of procedures including the positioning and placement of implanted catheters/sensors, extraction of permanently implanted leads and delivery of cardiovascular therapies. Optimal haptic rendering is achieved by using computational techniques to reconstruct the physically and perceptually relevant aspects of acquired signals and bridge the gap between the inserted catheter and operator's hand/catheter handle.

14 Claims, 23 Drawing Sheets

Related U.S. Application Data continuation-in-part of application No. 11/686,602, filed on Mar. 15, 2007, now Pat. No. 7,963,925, which is a continuation of application No. 11/584,465, filed on Oct. 20, 2006, now abandoned, which is a continuation-in-part of application No. 11/334,935, filed on Jan. 19, 2006, now abandoned, application No. 14/105,749, which is a continuation of application No. 13/448,879, which is a continuation of application No. 12/836,636, which is a continuation-in-part of application No. 12/245,058, filed on Oct. 3, 2008, now abandoned, which is a continuation-in-part of application No. 11/334,935, application No. 14/105,749, which is a continuation of application No. 13/448,879, which is a continuation of application No. 12/836,636, which is a continuation-in-part of application No. 11/848,346, filed on Aug. 31, 2007, now abandoned, which is a continuation-in-part of application No. 11/771,233, filed on Jun. 29, 2007, now abandoned, which is a continuation-in-part of application No. 11/746,752, filed on May 10, 2007, now abandoned, which is a continuation-in-part of application No. 11/334,935, application No. 14/105,749, which is a continuation of application No. 13/448,879, which is a continuation of application No. 12/836,636, which is a continuation-in-part of application No. 11/848,346, which is a continuation-in-part of application No. 11/746,752, which is a continuation-in-part of application No. 11/334,935, application No. 14/105,749, which is a continuation of application No. 13/448,879, which is a continuation of application No. 12/836,636, which is a continuation-in-part of application No. 11/848,346, which is a division of application No. 11/686,602, which is a continuation of application No. 11/584,465, which is a continuation-in-part of application No. 11/334,935, application No. 14/105,749, which is a continuation of application No. 13/448,879, which is a continuation of application No. 12/836,636, which is a continuation-in-part of application No. 11/848,346, which is a continuation-in-part of application No. 11/771,233, which is a continuation-in-part of application No. 11/746,752, application No. 14/105,749, which is a continuation of application No. 13/448,879, which is a continuation of application No. 12/836,636, said application No. 11/848,346 is a continuation-in-part of application No. 11/746,752, application No. 14/105,749, which is a continuation of application No. 13/448,879, which is a continuation of application No. 12/836,636.

(60) Provisional application No. 60/660,101, filed on Mar. 9, 2005, provisional application No. 60/647,102, filed on Jan. 26, 2005, provisional application No. 60/855,820, filed on Nov. 1, 2006, provisional application No. 61/270,924, filed on Jul. 15, 2009, provisional application No. 61/396,575, filed on May 29, 2010.

(56) References Cited

U.S. PATENT DOCUMENTS

| | | |
|---|---|---|
| 4,210,837 A | 7/1980 | Vasiliev et al. |
| 4,432,372 A | 2/1984 | Monroe |
| 4,844,062 A | 7/1989 | Wells |
| 5,389,865 A | 2/1995 | Jacobus et al. |
| 5,429,604 A | 7/1995 | Hammersmark et al. |
| 5,484,433 A | 1/1996 | Taylor et al. |
| 5,549,650 A | 8/1996 | Bornzin et al. |
| 5,576,727 A | 11/1996 | Rosenberg et al. |
| 5,609,607 A | 3/1997 | Hechtenberg et al. |
| 5,628,777 A | 5/1997 | Moberg et al. |
| 5,693,074 A | 12/1997 | Ferek Petric |
| 5,702,438 A | 12/1997 | Avitall |
| 5,769,640 A | 6/1998 | Jacobus et al. |
| 5,771,902 A | 6/1998 | Lee et al. |
| 5,833,623 A | 11/1998 | Mann et al. |
| 5,836,946 A | 11/1998 | Diaz et al. |
| 5,843,135 A | 12/1998 | Weijand et al. |
| 5,844,392 A | 12/1998 | Peurach et al. |
| 5,916,143 A | 6/1999 | Apple et al. |
| 5,944,022 A | 8/1999 | Nardella et al. |
| 5,959,613 A | 9/1999 | Rosenberg et al. |
| 5,971,931 A | 10/1999 | Raff |
| 6,059,759 A | 5/2000 | Mottola et al. |
| 6,070,100 A | 5/2000 | Bakels et al. |
| 6,077,236 A | 6/2000 | Cunningham |
| 6,096,004 A | 8/2000 | Meglan et al. |
| 6,104,158 A | 8/2000 | Jacobus et al. |
| 6,147,674 A | 11/2000 | Rosenberg et al. |
| 6,203,432 B1 | 3/2001 | Roberts et al. |
| 6,278,439 B1 | 8/2001 | Rosenberg et al. |
| 6,300,936 B1 | 10/2001 | Braun et al. |
| 6,304,777 B1 | 10/2001 | Ben-Haim et al. |
| 6,418,346 B1 | 7/2002 | Nelson et al. |
| 6,424,356 B2 | 7/2002 | Chang et al. |
| 6,429,849 B1 | 8/2002 | An et al. |
| 6,442,433 B1 | 8/2002 | Linberg |
| 6,480,745 B2 | 11/2002 | Nelson et al. |
| 6,526,984 B1 | 3/2003 | Nilsson et al. |
| 6,527,683 B2 | 3/2003 | Tolles |
| 6,572,560 B1 | 6/2003 | Watrous et al. |
| 6,574,511 B2 | 6/2003 | Lee |
| 6,622,045 B2 | 9/2003 | Snell et al. |
| 6,628,988 B2 | 9/2003 | Kramer et al. |
| 6,641,480 B2 | 11/2003 | Murzanski et al. |
| 6,685,732 B2 | 2/2004 | Kramer |
| 6,725,091 B2 | 4/2004 | Dal Molin |
| 6,740,033 B1 | 5/2004 | Olejniczak et al. |
| 6,746,972 B1 | 6/2004 | Kim et al. |
| 6,780,183 B2 | 8/2004 | Jimenez, Jr. et al. |
| 6,792,308 B2 | 9/2004 | Corbucci |
| 6,795,732 B2 | 9/2004 | Stadler et al. |
| 6,801,008 B1 | 10/2004 | Jacobus et al. |
| 6,804,559 B1 | 10/2004 | Kraus et al. |
| 6,805,667 B2 | 10/2004 | Christopherson et al. |
| 6,810,281 B2 | 10/2004 | Brock et al. |
| 6,816,301 B1 | 11/2004 | Schiller |
| 6,826,509 B2 | 11/2004 | Crisco, III et al. |
| 6,837,886 B2 | 1/2005 | Collins et al. |
| 6,863,943 B2 | 3/2005 | Wang et al. |
| 6,906,700 B1 | 6/2005 | Armstrong |
| 7,010,347 B2 | 3/2006 | Schecter |
| 7,063,671 B2 | 6/2006 | Couvillon, Jr. |
| 7,065,400 B2 | 6/2006 | Schechter |
| 7,091,948 B2 | 8/2006 | Chang et al. |
| 7,101,347 B2 | 9/2006 | Culhane et al. |
| 7,127,289 B2 | 10/2006 | Yu et al. |
| 7,139,621 B2 | 11/2006 | Gharsalli |
| 7,147,633 B2 | 12/2006 | Chee et al. |
| 7,154,470 B2 | 12/2006 | Tierling |
| 7,168,042 B2 | 1/2007 | Braun et al. |
| 7,176,892 B2 | 2/2007 | Kobayashi |
| 7,183,568 B2 | 2/2007 | Appenzeller et al. |
| 7,191,191 B2 | 3/2007 | Peurach et al. |
| 7,199,790 B2 | 4/2007 | Rosenberg et al. |
| 7,206,633 B2 | 4/2007 | Saba |
| 7,209,117 B2 | 4/2007 | Rosenberg et al. |
| 7,218,310 B2 | 5/2007 | Tierling et al. |
| 7,225,404 B1 | 5/2007 | Zilles et al. |
| 7,257,447 B2 | 8/2007 | Cates et al. |
| 7,266,832 B2 | 9/2007 | Miller |
| 7,316,681 B2 | 1/2008 | Madhani et al. |
| 7,331,967 B2 | 2/2008 | Lee et al. |
| 7,333,643 B2 | 2/2008 | Murphy et al. |
| 7,369,115 B2 | 5/2008 | Cruz-Hernandez et al. |
| 7,386,365 B2 | 6/2008 | Nixon |

(56) References Cited

U.S. PATENT DOCUMENTS

| | | |
|---|---|---|
| 7,426,412 B1 | 9/2008 | Schecter |
| 7,623,114 B2 | 11/2009 | Rank |
| 7,639,232 B2 | 12/2009 | Grant et al. |
| 7,653,436 B2 | 1/2010 | Schecter |
| 7,656,388 B2 | 2/2010 | Schena et al. |
| 7,689,283 B1 | 3/2010 | Schecter |
| 7,701,438 B2 | 4/2010 | Chang et al. |
| 7,720,529 B1 | 5/2010 | Schecter |
| 7,725,214 B2 | 5/2010 | Diolaiti |
| 7,740,627 B2 | 6/2010 | Gammie et al. |
| 7,751,888 B1 | 7/2010 | Schecter |
| 7,751,889 B1 | 7/2010 | Schecter |
| 7,762,985 B2 | 7/2010 | Kabrick et al. |
| 7,765,333 B2 | 7/2010 | Cruz-Hernandez et al. |
| 7,770,262 B2 | 8/2010 | Schultz et al. |
| 7,779,166 B2 | 8/2010 | Grant et al. |
| 7,780,651 B2 | 8/2010 | Madhani et al. |
| 7,791,588 B2 | 9/2010 | Tierling et al. |
| 7,794,455 B2 | 9/2010 | Abboud et al. |
| 7,805,194 B1 | 9/2010 | Schecter |
| 7,821,493 B2 | 10/2010 | Tierling et al. |
| 7,821,498 B2 | 10/2010 | Kramer et al. |
| 7,843,158 B2 | 11/2010 | Prisco |
| 7,850,642 B2 | 12/2010 | Moll et al. |
| 7,865,269 B2 | 1/2011 | Prisco et al. |
| 7,898,156 B2 | 3/2011 | Wang et al. |
| 7,924,144 B2 | 4/2011 | Makinen et al. |
| 7,931,586 B2 | 4/2011 | Brock et al. |
| 7,942,868 B2 | 5/2011 | Cooper |
| 7,947,050 B2 | 5/2011 | Lee et al. |
| 7,947,051 B2 | 5/2011 | Lee et al. |
| 7,963,288 B2 | 6/2011 | Rosenberg et al. |
| 7,963,925 B1 | 6/2011 | Schecter |
| 7,969,288 B2 | 6/2011 | Braun et al. |
| 7,970,469 B2 | 6/2011 | Schecter |
| 7,972,298 B2 | 7/2011 | Wallace et al. |
| 7,974,681 B2 | 7/2011 | Wallace et al. |
| 7,978,183 B2 | 7/2011 | Rosenberg et al. |
| 7,979,146 B2 | 7/2011 | Ullrich et al. |
| 7,982,588 B2 | 7/2011 | Makinen et al. |
| 7,982,720 B2 | 7/2011 | Rosenberg et al. |
| 8,000,825 B2 | 8/2011 | Ullrich et al. |
| 8,003,982 B2 | 8/2011 | Wang et al. |
| 8,004,229 B2 | 8/2011 | Nowlin et al. |
| 8,010,180 B2 | 8/2011 | Quaid et al. |
| 8,014,864 B2 | 9/2011 | Schecter et al. |
| 8,016,818 B2 | 9/2011 | Ellis et al. |
| 8,026,798 B2 | 9/2011 | Makinen et al. |
| 8,032,212 B2 | 10/2011 | Bornzin et al. |
| 8,039,834 B2 | 10/2011 | Wang et al. |
| 8,041,413 B2 | 10/2011 | Barbagli et al. |
| 8,043,351 B2 | 10/2011 | Yon et al. |
| 8,050,760 B2 | 11/2011 | Cholette |
| 8,059,105 B2 | 11/2011 | Rosenberg et al. |
| 8,090,444 B2 | 1/2012 | Min et al. |
| 8,156,809 B2 | 4/2012 | Tierling et al. |
| 8,174,373 B2 | 5/2012 | Makinen et al. |
| 8,209,012 B2 | 6/2012 | Schecter |
| 8,211,032 B2 | 7/2012 | Schecter et al. |
| 8,214,039 B1 | 7/2012 | Schecter |
| 8,292,797 B2 | 10/2012 | Chapman et al. |
| 8,663,122 B2 | 3/2014 | Schecter |
| 2002/0015950 A1 | 2/2002 | Jones et al. |
| 2002/0026103 A1 | 2/2002 | Norris et al. |
| 2002/0072784 A1 | 6/2002 | Sheppard et al. |
| 2002/0120188 A1 | 8/2002 | Brock et al. |
| 2002/0183738 A1 | 12/2002 | Chee et al. |
| 2003/0006669 A1 | 1/2003 | Pei et al. |
| 2003/0083702 A1 | 5/2003 | Stadler et al. |
| 2003/0187362 A1 | 10/2003 | Murphy et al. |
| 2003/0216620 A1 | 11/2003 | Jain et al. |
| 2004/0019285 A1 | 1/2004 | Eigler et al. |
| 2004/0068199 A1 | 4/2004 | Echauz et al. |
| 2004/0111127 A1 | 6/2004 | Gliner |
| 2004/0153128 A1 | 8/2004 | Suresh et al. |
| 2004/0167587 A1 | 8/2004 | Thompson |
| 2004/0172079 A1 | 9/2004 | Chinchoy |
| 2004/0176679 A1 | 9/2004 | Murphy et al. |
| 2004/0176810 A1 | 9/2004 | Stadler et al. |
| 2004/0186465 A1 | 9/2004 | Francischelli et al. |
| 2004/0231100 A1 | 11/2004 | Schultz et al. |
| 2005/0043895 A1 | 2/2005 | Schechter |
| 2005/0059876 A1 | 3/2005 | Krishnan et al. |
| 2005/0113886 A1 | 5/2005 | Fischell et al. |
| 2005/0182447 A1 | 8/2005 | Schecter |
| 2005/0241026 A1 | 10/2005 | Esler et al. |
| 2005/0262676 A1 | 12/2005 | Kim et al. |
| 2005/0280508 A1 | 12/2005 | Mravca et al. |
| 2006/0059997 A1 | 3/2006 | Kim et al. |
| 2006/0083720 A1 | 4/2006 | Fraser et al. |
| 2006/0114088 A1 | 6/2006 | Shachar |
| 2006/0159747 A1 | 7/2006 | Schumacher et al. |
| 2006/0161045 A1 | 7/2006 | Merril et al. |
| 2006/0167529 A1 | 7/2006 | Schecter |
| 2006/0276775 A1 | 12/2006 | Rosenberg et al. |
| 2007/0021977 A1 | 1/2007 | Elsholz |
| 2007/0043338 A1 | 2/2007 | Moll et al. |
| 2007/0103437 A1 | 5/2007 | Rosenberg |
| 2007/0156123 A1 | 7/2007 | Moll et al. |
| 2007/0173861 A1 | 7/2007 | Strommer et al. |
| 2007/0191901 A1 | 8/2007 | Schecter |
| 2007/0197896 A1 | 8/2007 | Moll et al. |
| 2007/0197939 A1 | 8/2007 | Wallace et al. |
| 2007/0233044 A1 | 10/2007 | Wallace et al. |
| 2008/0009750 A1 | 1/2008 | Aeby et al. |
| 2008/0009759 A1 | 1/2008 | Chetham |
| 2008/0009791 A1 | 1/2008 | Cohen et al. |
| 2008/0010705 A1 | 1/2008 | Quaid et al. |
| 2008/0067618 A1 | 3/2008 | Wang et al. |
| 2008/0119871 A1 | 5/2008 | Brock et al. |
| 2008/0218770 A1 | 9/2008 | Moll et al. |
| 2008/0262513 A1 | 10/2008 | Stahler et al. |
| 2008/0275367 A1 | 11/2008 | Barbagli et al. |
| 2008/0288013 A1 | 11/2008 | Schecter |
| 2008/0290040 A1 | 11/2008 | Kane et al. |
| 2008/0303782 A1 | 12/2008 | Grant et al. |
| 2009/0012533 A1 | 1/2009 | Barbagli et al. |
| 2009/0024141 A1 | 1/2009 | Stahler et al. |
| 2009/0030332 A1 | 1/2009 | Schecter |
| 2009/0062602 A1 | 3/2009 | Rosenberg et al. |
| 2009/0066195 A1 | 3/2009 | Wang et al. |
| 2009/0076476 A1 | 3/2009 | Barbagli et al. |
| 2009/0123111 A1 | 5/2009 | Udd |
| 2009/0138025 A1 | 5/2009 | Stahler et al. |
| 2009/0167677 A1 | 7/2009 | Kruse et al. |
| 2009/0177095 A1 | 7/2009 | Aeby et al. |
| 2009/0179523 A1 | 7/2009 | Wang et al. |
| 2009/0243997 A1 | 10/2009 | Tierling et al. |
| 2009/0259280 A1 | 10/2009 | Wilkin et al. |
| 2009/0299431 A1 | 12/2009 | Schecter |
| 2009/0301196 A1 | 12/2009 | Wang et al. |
| 2009/0312814 A1 | 12/2009 | Schecter et al. |
| 2010/0013761 A1 | 1/2010 | Birnbaum et al. |
| 2010/0017759 A1 | 1/2010 | Birnbaum et al. |
| 2010/0045619 A1 | 2/2010 | Birnbaum et al. |
| 2010/0049060 A1 | 2/2010 | Schecter |
| 2010/0056851 A1 | 3/2010 | Wang et al. |
| 2010/0063478 A1 | 3/2010 | Selkee |
| 2010/0073150 A1 | 3/2010 | Olson et al. |
| 2010/0114115 A1 | 5/2010 | Schlesinger et al. |
| 2010/0117488 A1 | 5/2010 | Wang et al. |
| 2010/0121403 A1 | 5/2010 | Schecter et al. |
| 2010/0123588 A1 | 5/2010 | Cruz Hernandez et al. |
| 2010/0152620 A1 | 6/2010 | Ramsay et al. |
| 2010/0152795 A1 | 6/2010 | Schecter |
| 2010/0152796 A1 | 6/2010 | Schecter |
| 2010/0179587 A1 | 7/2010 | Grant et al. |
| 2010/0228103 A1 | 9/2010 | Schecter |
| 2010/0234913 A1 | 9/2010 | Schecter |
| 2010/0283731 A1 | 11/2010 | Grant et al. |
| 2010/0312129 A1 | 12/2010 | Schecter |
| 2011/0006286 A1 | 1/2011 | Wang et al. |
| 2011/0043454 A1 | 2/2011 | Modarres et al. |
| 2011/0050405 A1 | 3/2011 | Hollis, Jr. et al. |

(56) References Cited

U.S. PATENT DOCUMENTS

| | | | |
|---|---|---|---|
| 2011/0090070 | A1 | 4/2011 | Modarres et al. |
| 2011/0121953 | A1 | 5/2011 | Grant et al. |
| 2011/0166513 | A1 | 7/2011 | Cohen et al. |
| 2011/0184406 | A1 | 7/2011 | Selkee |
| 2011/0193824 | A1 | 8/2011 | Modarres et al. |
| 2011/0230896 | A1 | 9/2011 | Wallace et al. |
| 2011/0238083 | A1 | 9/2011 | Moll et al. |
| 2011/0275947 | A1 | 11/2011 | Feldman et al. |
| 2011/0306890 | A1 | 12/2011 | Schecter et al. |
| 2012/0265076 | A1 | 10/2012 | Schecter |
| 2012/0265083 | A1 | 10/2012 | Schecter |
| 2013/0274712 | A1 | 10/2013 | Schecter |
| 2013/0321262 | A1 | 12/2013 | Schecter |
| 2014/0207010 | A1 | 7/2014 | Schecter |

FOREIGN PATENT DOCUMENTS

| | | | |
|---|---|---|---|
| WO | WO2006/081132 | A2 | 8/2006 |
| WO | WO2006/081132 | A3 | 11/2007 |
| WO | WO2010/129892 | A2 | 11/2010 |
| WO | WO2011/005814 | A1 | 1/2011 |
| WO | WO2011/022319 | A1 | 2/2011 |
| WO | WO2011/046714 | A1 | 4/2011 |
| WO | WO2011/097356 | A1 | 8/2011 |

OTHER PUBLICATIONS

U.S. Appl. No. 60/660,101, filed Mar. 9, 2005.
U.S. Appl. No. 11/584,465, filed Oct. 20, 2006, Abandoned.
U.S. Appl. No. 11/746,752, filed May 1, 2007, Abandoned.
U.S. Appl. No. 11/771,233, filed Jun. 29, 2007, Abandoned.
U.S. Appl. No. 11/848,346, filed Aug. 31, 2007, Abandoned.
U.S. Appl. No. 61/628,551, filed Nov. 2, 2011.
U.S. Appl. No. 61/655,804, filed Jun. 5, 2012.
U.S. Appl. No. 60/855,820, filed Nov. 1, 2006.
U.S. Appl. No. 61/270,924, filed Jul. 15, 2009.
U.S. Appl. No. 61/396,575, filed May 29, 2010.
U.S. Appl. No. 61/341,129, filed Mar. 27, 2010.
Makoto Shimojo et al., A High-Speed Mesh of Tactile Sensors Fitting Arbitrary Surfaces, IEEE Sensor Journal, vol. 10, No. 4, Apr. 2010.
Allison M. Okamura et al., Reality-Based Models for Vibration Feedback in Virtual Environments, IEEE/ ASME Transactions on Mechatronics, vol. 6, No. 3, Sep. 2001.
Office Action issued in related U.S. Appl. No. 11/746,752, Mailed Apr. 5, 2010.
Farrokh Janabi-Sharifi et al., Discrete-Time Adaptive Windowing for Velocity Estimation, IEEE/ASME Transactions on Control Systems Technology, vol. 8, No. 6, Nov. 2000.
Young Qin et al., Microfibre-nanowire Hybrid Structure for Energy Scavenging, School of Materials Science and Engineering, Georgia Institute of Technology, Atlanta, Georgia, USA, vol. 451, Feb. 2008.
S. Stramigioli et al., A Novel Theory for Sample Data System Passivity, IEEE/RSJ, International Conference of Intelligent Robots and Systems, EPFL, Lausanne, Switzerland, Oct. 2002.
Honjie Leng et al., Development of a Novel Deformation-Based Tissue Softness Sensor, IEEE Sensors Journal, vol. 9, No. 5, May 2009.
J. E. Colgate et al., Factors Affecting the Z-Width of a Haptic Display, IEEE, Department of Mechanical Engineering, Northwestern University, 2145 Sheridan Rd., Evanston, Illinois, 1994.
J. E. Colgate et al., Passivity of a Class of Sampled-Data Systems: Application to Haptic Interfaces, IEEE, Department of Mechanical Engineering, Northwestern University, Evanston, IL, Journal of Robotic Systems, John Wiley & Sons Inc, 1997.
Dipen C. Shah et al., Area Under the Real-Time Contact Force Curve (Force-Time Integral) Predicts Radiofrequency Lesion Size in an In Vitro Contractile Model, Journal of Cardiovascular Electrophysiology, vol. No. 10, pp. 1-5, 2010.
Office Action issued in the related U.S. Appl. No. 11/686,602 mailed Jun. 24, 2010.

Excerpts, Heart Rhythm, vol. 2, No. 5, May Supplement, 2005 including Schecter S et al. The Effects of Atrial Flutter on Left Ventricular Rotation: A Tissue Doppler Study. Heart Rhythm Society 2005; 2(1S): S134.
Dissertation of Katherine Julianne Kuchenbecker, Characterizing and Controlling the High Frequency Dynamics of Haptic Devices. PhD Thesis Stanford University Department of Mechanical Engineering. 2006.
Giovanni B. Perego et al. "Simultaneous vs. sequesntial biventricular pacing in dilated cardiomyopathy . . . ", The European Journal of Heart Failure, 5, 2003, pp. 305-313.
Carlo Pappone et al."Cardiac Contractility Modulation by Electric Currents Applied During the Refractory Period in Patiens . . . ",The American Journal of Cardiology, V.90, Dec. 2002.
P. Ritter et ai."Determination of the optimal atrioventricular delay in DOD pacing, Comparison between echo and peak endocardial measurements", Europace, 1999, 1, pp. 126-130.
Jaroslav Meluzin et ai."A fast and simple echacardiographic method of determination of the optimal atrioventricular delay in patients after . . . " Pace, Jan. 2004,vol. 27.
Ric Willems et al. "Nonexcitatory stimulation as a novel treatment for heart failure: cause for excitement?" European Heart Journal, 2004, 25, pp. 626-628.
James D. Thomas et al. "Digital Echocardiography 2002: Now is the Time" Journal of the American Society of Echocardiography, Aug. 2002.
C-M Yu et al."High prevalence of left ventricular systolic and diastolic asynchrony in patients with confestive heart failure and normal QRS duration" Heart, 2003;89,pp. 54-60.
Carlo Pappone et al."First Human Chronic Experience With Cardiac Contractility Modulation by Nonexcitatory . . . " Journal of Cardiovascular Electrophysiology, vol. 15, 4, 2004.
Dipla, K. et ai."The Sarcoplasmic Reticulum and the Na+/Ca2+ Exchanger Both Contribute to theCa 2+ Transient of Failing Human Ventricular . . . ", Circulation Research, 1999;84.
Padeletti et al."Digital Technology for Cardiac Pacing" The American Journal of Cardiology, vol. 95, Feb. 15, 2005, pp. 479-482.
Harvey Feigenbaum "Digital Echocardiography", Excerpta Medica, Inc., 2000, 2G-3G.
Burknoff et al. "Electric Currents Applied During rhe Refractory Period Can Modulate Cardiac Contractility in Vitro and in Vivo", Heart Failure Previews, 6, 2001, pp. 27-34.
PCT Search Report from International Application No. PCT/US06/01946; search report completed Apr. 27, 2007 and mailed Aug. 15, 2007.
Office Action issued in a corresponding U.S. Appl. No. 11/848,346, Dec. 22, 2010.
Zhong Y et. al. An electromechanical based deformable model for soft tissue simulation. Artificial Intelligence in Medicine. Nov. 2009; vol. 47, 3, pp. 275-288.
Controlling a Heart Simulator with CompactRIO and LabVIEW, http://sine.ni.com/cs/app/doc/p/id/cs-13021, as accessed on Feb. 13, 2013.
Chubb EC et al. ShiverPaD: A Glass Haptic Surface That Produces Shear Force on a Bare Finger. IEEE Transactions on Haptics 2010, vol. 3, No. 3, pp. 189-198.
Gleeson BT et al. Perception of Direction for Applied Tangential Skin Displacement: Effects of Speed, Displacement, and Repetition. IEEE Transactions on Haptics 2010, vol. 3, No. 3 pp. 177-188.
Mafi R, et. al. A parallel Computing Platform for Real-Time Haptic Interaction with Deformable Bodies. IEEE Transactions on Haptics 2010, vol. 3, No. 3. p. 211-223.
Frisoli A. et al. Kinematic Design of a Two Contact Points Haptic Interface for the Thumb and Index Fingers of the Hand. ASME J Mechanical Design, vol. 129, pp. 520-529, 2007.
Proctor RW et al. Implications of Compatibility and Cuing Effects for Multimodal Interfaces. Proc. Int'l Conf. Human-Computer Interaction, vol. 11, 2005.
Easton RD et. al. Transfer between Vision and Haptics: Memory for 2D Patterns and 3D Objects. Psychonomic Bull. and Rev., vol. 4, pp. 322-325, 1997.
Ahmaniemi T, et al. Design of Dynamic Vibrotactile Textures. IEEE Transactions on Haptics, vol. 3, No. 4. p. 245-256, Oct.-Dec. 2010.

(56) References Cited

OTHER PUBLICATIONS

Gleeson BT, et al. Design of a Fingertip-Mounted Tactile Display with Tangential Skin Displacement Feedback. IEEE Transactions on Haptics, vol. 3, No. 4. p. 297-298, Oct.-Dec. 2010.
Ikeda A. et al., Electrogram Prameters (Injury current, amplitude, dV/dt) and Impedance are poor predictors of electrode-tissue contact force for Radiofrequency Ablation. Heart Rhythm Society, May 2008, Abstract 4570, PO5-41.
Burdea, GC., Force and Touch Feedback for Virtual Reality. New York: Wiley Interscience, 1996, Abstract.
Nguyen, CTC, IEEE Spectrum Dec. 2009.
Hannaford B. et al. Stable Control of Haptics. In Touch in Virtual Environments: Proceedings USC Workshop on Haptic Interfaces, edited by Margret McLaughlin. Upper Saddle River, JN; Prentice Hall, 2001.
Abbott JJ, Okamura AM, Effects of Position Quantization and Sampling Rate on Virtual Wall Passivity, IEEE Transactions on Robotics 12:5 (2005), 952-964.
Salcudean SE, and Vlaar TD, On the Emulation of Stiff Walls and Static Friction with a Magneticaly Levitated Input/Output Device. 1996.
Immersion, Touchsense Tactile Feedback, http://www.immersion.com/products/touchsense-tactile-feedback/index.html, as accessed on Feb. 13, 2013.
DuraAct™ Piezoelectric Patch Transducers for Industry and Research, http://www.pi-usa.us/pdf/PI_Catalog_DuraAct_Piezo_Patch_Transducer_Piezo_Composite_C1.pdf, as accessed on Feb. 13, 2013.
Otaduy MA., "Haptic Rendering; Foundations, Algorithms and Applications." A.K. Peters Ltd. 2008. p. 138-147, 440.
Kawai M., and Yoshikawa T., Haptic Display of Movable Virtual Object with Interface Device Capable of Continuous-Time Impedance Display by Analog Circuit. In IEEE International Conference on Robotics and Automation, pp. 229-234, Washington, DC: IEEE Computer Society 2002.
Bracke, F., Neth Heart J 2008;16(Suppl1): S28-S31.
Coyne KS, Paramore C, Grandy S, Mercader M, Reynolds MR, Zimetbaum P. Assessing the direct costs of treating nonvalvular arterial fibrillation in the United States. *Value Health,* 2006;9:348-356. [PubMed].
Kozak LJ, Lees KA, DeFrances CJ. National Hospital Discharge Survey: 2003 Annual summary with detailed diagnosis and procedure data. *Vital Health Stat.* 2006:1-206.
Go AS, Hylek EM, Phillips KA, Chang Y, Henault LE, Selby JV, Singer DE. Prevalence of diagnosed atrial fibrillation in adults: National implications for rhythm management and stroke prevention. The anticoagulation and risk factors in atrial fibrillation (ATRIA) study. *JAMA* 2001;285:2370-2375.
Miyasaka Y, Barnes ME, Gersh BJ, Cha SS, Bailey KR, Abhayaratna WPS JB, Tsang TSM. Secular trends in incidence of atrial fibrillation in Olmstead County, Minnesota, 1980 to 2000, and implications on the projections for future prevalence. *Circulation,* 2006;114:119-124.
Wattigney WA, Mensah GA, Croft JG. Increasing trends in hospitalization for atrial fibrillation in the United States, 1985 through 1999. *Circulation.* 2003;108:711-716.
Bentkover JD, Stewart EJ, Ignaszewski A, Lepage S, Liu P, Cooper J. *Int J. Cardiol.* Mar. 2003;88(1):33-41. New Technologies and potential cost savings related to morbidity and mortality reduction in Class II/IV heart failure patients in Canada.
Ho KK, Pinsky JL, Kannel WB, Levy D. *J Am Coll Cardiol.* Oct. 1993;22(4 Suppl a):6A-13A. The epidemiology of heart failure: the Framingham Study.
http://www.intertechnology.com/Trans_Tek/TransTek_Series_100.html, as accessed on Feb. 11, 2013.
Tavakoli M. et al. Haptics for Teleoperated Surgical Robotic Systems. pp. 13-30. *World Scientific Publishing Company* 2007.
V Dambrauskaite, et al. "The Evaluation of Pulmonary Hypertension Using Right Ventricular Myocardial Isovolumic Relaxation Time", *J. Am. Soc. Echo.* 2005, 18:1113-20.

P. Caso, et al. "Association between myocardial right ventricular relaxation time and pulmonary atrial pressure in chronic obstructive lung disease analysis by Pulsed Doppler tissue imaging". *J. Am. Echo.* 2001, 14:970-77.
Guido Dehnhardt, Björn Mauck & Horst Bleckmann. *Nature* 394, 235-236 (Jul. 16, 1998) | doi:10.1038/28303.
Ansalone et al., *JACC 2002.*
Bordacher et al., *JACC 2004;* Dec. 7.
Sogaard, *J. Am Coll Cardiol,* 2002. 40: p. 723-720.
Van Gelder, Berry M., Bracke, Frank A., Meijer, Albert, Lakerveld, Lex JM, Pijls, Nico HJ, "Effect of optimiaing the VV interval on left ventricular contractility in cardiac resynchronization therapy." *Am J Cardiol,* 2004. 93: p. 1500-1503.
Villard E, Dubosscq-Bidot L, Charron P, et al. *Eur Heart J* 2005; 26:795-803.
Daruwala RS, Rudra A, Ostrer H, et al., "A versatile statistical analysis algorithm to detect genome copy number variation:" *Proceedings of the National Academy of Sciences of the United States of America,* Nov. 16, 2004; 101 (46): 16292-7.
Breast Cancer Risk Assessment Tool, http://www.cancer.gov/bcrisktool/, as accessed on Feb. 11, 2013.
Gail Model and NSABP Model, http://www.halls.md/breast/riskcom.htm, as accessed on Feb. 11, 2013.
Selker et al., Patient specific predictions of outcomes in myocardial infarction for real-time emergency use: a thrombolytic predictive instrument. *Ann Intern Med* 1997; 127: 538-56.
Zhang Q. et al., "Assessment of the Effect of Cardiac Resynchronization Therapy on Intraventricular Mechanical Sychronicity be Regional Volumetric Changes." *Am J Cardiol* 2005; 95: 126-129.
Saxon LA, Ellenbogen KA. "Resynchronization Therapy for the Treatment of Heart Failure." *Circulation* 2003; 108: 1044.
Santomauro M et al. "Left ventricular pacing in patients with heart failure: evaluation study with Fourier analysis of radionuclide venticulography." *Ital Heart J* 2004; 5 (12): 906-911.
U.S. Appl. No. 60/634,165, filed Dec. 8, 2004.
Sinnamon LJ, Saad MM, Bowman RM, Gregg JM. "Exploring grain size as a cause for "dead-Layer" effects in thin film capacitors." *Appl. Phys. Lett.* 2002. 81, 703-705.
Sai N. Kolpak AM, Rappe AM. "Ferroelectricity in ultra-thin perovskite films." *Phys. Rev.* 2005. B 72, 020101R.
Shiyou Xu et al 2006 Nanotechnology 17 4497-4501, doi:10.1088/0957-4484/17/17/036.
Nanosprings: Helical Piexoelectric Nanostruxtures Could be Actuators & Transducers in Future Nanosystems, Georgia Tech Research News, http://gtresearchnews.gatech.edu/newsrelease/nanosprings.htm, Oct. 16, 2003.
Carbon nanotube, http://en.wikipedia.org/wiki/carbon_nanotubes, as accessed on Feb. 11, 2013.
Nanotubes-101 Presentation, http://www.cheaptubesinc.com/Carbon-Nanotubes-101.htm, as accessed on Feb. 11, 2013.
Yang, S., Researchers create first ever integrated silicon circuit with nanotube transistors, http://www.berkeley.edu/news/media/releases/2004/01/05_nano.shtml, Jan. 5, 2004.
Philip G. Collins and Phaedon Avouris (2000), Nanotubes for Electronics—*Scientific American* Dec. 2000, 62-69.
Wittkampf FHM et al. "LocalLisa, New Technique for Real Time 2 Dimensional Localization of Regular Intracardiac Electrodes." *Circulation* 1999; 99: 1312-1317.
Packer DL, "Three-Dimensional Mapping of Intervential Electrophysiology: Techniques and Technology." Journal of Cardiovascular Electrophysiology 2005; vol. 16, No. 10, 1110-1117.
Packer DL, "Evolution and mapping and anatomic imaging of cardiac arrhythmias." J Cardiovasc Electrophysiol 2004; 15: 839-854.
Gruner, G., "Carbon Nanotube Films for Transparent and Plastic Electronics." *Journal of Materials Chemistry* 2006, vol. 16, No. 35, pp. 3533-3539.
Gruner, G., "Carbon Nanotube Transistors for Biosensing Applications." *Analytical and Bioanaoytical Chemistry* 2006. vol. 384, pp. 322-335.
Ou, Fung Suong; *Applied Physics Letters* Dec. 2006.
http://bios.ewi.utwente.nl/, as accessed on Feb. 11, 2013.
http://www.mic.dtu.dk/, as accessed on Feb. 11, 2013.
http://www.eng.monash.edu.au/mnrl, as accessed on Feb. 13, 2013.

(56) References Cited

OTHER PUBLICATIONS http://www.appchem.t.u-tokyo.ac.jp/index_e.html, as accessed on Feb. 13, 2013.

http://biomems.uwaterloo.ca/index.html, as accessed on Feb. 11, 2013.

Hocini M, Sanders P, Jais P et al. "Techniques for Curative Treatment of Atrial Fibrillation." *Journal of Cardiovascular Electrophysiology*, vol. 15, No. 12, Dec. 2004, p. 1467.

Oral H, Pappone C, Chugh A. "Circumferential Pulmonary Vein Ablation for Chronic Atrial Fibrillation." *NEJM* 354:9, Mar. 2, 2006, p. 934.

Nademmanee K, Mckenzie J, Koar E, et al. "A New Approach for Catheter Ablation of Atrial Fibrillation: Mapping of the Electrophysiologic Substrate." *JACC* vol. 43, No. 11, 2004. p. 2044.

Gonzalez MD, Otomo K, Shah N. "Transeptal Left Heart Catheterization for Cardiac Ablation Procedures." *J Interventional Cardiac Electrophysiology* 2001. 5, 89-95.

Pappone C, Santinelli V. "The Who, What, Why and How-to Guide for Circumferential Pulmonary Vein Ablation." *J Cardiovascular Electrophysiology* 2004. vol. 15, 1226-1230.

*Circulation.* 2001;104:2118.

Schecter et al. "Guiding Catheters with Side Holes Relieve Pressure Damping and Improve Coronary Blood Flow: Assessment with the Doppler Flowire." *Circulation* 1994; 90: 4, Part 2: 1-164.

Kaneko M, Kanayama N, Tsuji T. "Active Antenna for Contact Sensing." *IEEE Transactions on Robotics and Automation*, vol. 14, No. 2, Apr. 1998. 278-291.

Neimark MA, Andermann JL, Hopfield JJ, Moore CI. "Vibrissa Resonance as a Transduction Mechanism for Tactile Encoding." *J Neurosci*, Jul. 23, 2003. 23(16): 6499-6509.

Hartmann MJ, Johnson NJ, Towal RB, Assad C. "Mechanical Characteristics of Rat Vibrissae: Resonant Frequencies and Damping in Isolated Whiskers and in the Awake Behaving Animal." *J Neurosci*, Jul. 23, 2003. 23(16): 6510-6519.

Krupa DJ, Matell MS, Brisben AJ, Oliveira LM, Nicolelis MAL. "Behavorial Properties of the Trigeminal Somatosensory System in Rats Performing WhickerDependent Tactile Discriminations." *J Neurosci*, Aug. 1, 2001, 21(15): 5752-5763.

Solomon JH, Hartmann MJ. "Robotic whiskers used to sense features." *Nature* 2006, vol. 443, 525.

Hsu, JWR et al. "Directed spatial organization of zinc oxide nanorods." *Nano Lett.* 5, 83-86 (2005).

Yoshida N et al. "Validation of Transthoracic Tissue Doppler Assessment of Left Atrial Appendage Function." *J Am Soc Echocardiography* 2007; 20: 521-526.

Dubin et al. "Carbon nanotube Fibers are Compatible With Mammalian Cells and Neurons." *IEEE Transactions on Nanobioscience*, vol. 7, No. 1, Mar. 2008.

Berkelmann PJ, Whitcomb L, Taylor et al. A miniature microsurgical instrument tip force sensor for enhanced force feedback during robot-assisted manipulation. *IEEE Transactions on Robotics and Automation 2003*, 19 (5), 917-922.

Ezhilvalavan S. et al., *J. Phys* 2006. Conf. Ser. 34 979-984.

Stampfer, D.; Jungen, A.; Hierold, C. Sensors, 2004. *Proceedings of IEEE*. Volume , Issue , Oct. 24-27, 2004, pp. 1056-1059 vol. 2.

Singh et al. *Nanotechnology* 2007, 18 475501, abstract.

Hwang, J.D.; Williams, M.D.; Niemeyer, G. Proceedings. 12th International Symposium on Haptic Interfaces for Virtual Environment and Teleoperator Systems, 2004. HAPTICS apos; 04 Volume, Issue, Mar. 27-28, 2004 pp. 24-31.

Sharifi F, Hayward V, Chen CJ. "Discrete-Time Adaptive Windowing for Velocity Estimation." IEEE Transactions on Control Systems Technology 8:6 (2000), 1003-1009.

Rougeron, M. et al. "A Control Approach for Real Time Human Grasp Simulation with Deformable Fingertips." *Intelligent Robots and Systems*, 2006 IEEE/RSJ International Conference Oct. 9-15, 2006 pp. 4634-4640.

Demersseman R et al. "Magnetorhelogical Brake for Haptic Rendering Haptics: Perception, Devices and Scenarios." 6th International Conference, Eurohaptics 2008, Madrid, Spain, Jun. 2008 Proceedings, pp. 940-945.

Khuri-Yakub et al. "Next-Gen Ultrasound." IEEE Spectrum, vol. 46, No. 5, p. 44-54, May 2009.

Campion G, and Hayward V. "Fundamental Limits in the Rendering of Virtual Haptic Textures." In Proc of the World Haptics Conference. pp. 263-270. Washington DC. IEEE Computer Society 2005.

McNeely et al. "Six Degree of Freedom Haptic Rendering using Voxel Sampling." In Proceedings of SIGGRAOH 99, Computer Graphics Proceedings, Annual Conference Series, Edited by Alyn Rockwood. pp. 401-408. Reading, MA: Addison Wesley Longman 1999.

Moreau JJ, and Jean M. "Numerical Treatment of Contact and Friction: the Contact Dynamics Method." Engineering Systems Design and analysis 4 (1996), 201-208.

Chuang J et al. Embeddable wireless strain sensor based on resonant RF carivites. Rev. Sci. Instrum., vol. 76, No. 9, p. 094703, 2005.

Rizzoli V, et al. A New Wireless Displacement Sensor Based on Reverse Design of Microwave and Millimeter-Wave antenna Array. IEEE Sensors Journal, vol. 9, No. 11, Nov. 2009. p. 1557.

Pulmonary Vein Stenosis Complicating Ablation for Atrial Fibrillation: Clinical Spectrum and Interventional Considerations. David R. Holmes, Jr.J Am Coll Cardiol Intv, 2009; 2:267-276.

Pulmonary Vein Anatomy in Patients Undergoing Catheter Ablation of Atrial Fibrillation: Lessons Learned by Use of Magnetic Resonance Imaging. Kato R et al. Circulation. 2003; 107: 2004-2010.

Incidence and Predictors of Pulmonary Vein Stenosis Following Catheter Ablation of Atrial Fibrillation using the Anatomic Pulmnoary Vein Ablation Approach: Results from Paired Magnetic Resonance Imaging. Dong J et al. J Cardiovasc Electrophysiol 2005, vol. 16, pp. 845-852.

Dill T et al. Circulation 2003;107, 845-850.

Sorgente, A. et al. Europace (2011) 13 (2): 205-212.

Tomotsugu T et al. J Am Coll Cardiol, 2003; 41:1243-1250.

Robbins IM, Colvin EV, Doyle TP, et al. Pulmonary vein stenosis after catheter ablation of atrial fibrillation. Circulation. 1998; 98:1769-1775.

Tsao HM et al. J Cardiovasc Electrophysiol 2010; 21: 270-277.

S. Sherrit, G. Yang, H.D. Wiederick and B.K. Mukherjee, Temperature Dependence of the Dielectric, Elastic, Piezoelectric Material Constants of Lead Zirconate Titanate Ceramics, http://mastersonics.com/documents/mmm_basics/general_info/ultrasonics_faq/ferro29.p. df, 1999.

Hansoo Kim and Wolfgang Sigmund. Zinc oxide nanowires on carbon nanotubes. Appl. Phys. Lett. 81, 2085 (2002).

Kern TA. Engineering Haptic Devices. (Ed.) 2009, XXXI, 472 p. 243-276.

Tanaka, Y.; Doumoto, K.; Sano, A.; Fujimoto, H.; , "Development of a sensor system with syringe based on tactile sensing using balloon expansion," Robotics and Automation (ICRA), 2010 IEEE International Conference on , vol., No., pp. 4861-4866, May 3-7, 2010.

Tabata, T. et al. J Am Coll Cardiol, 2003; 41:1243-1250.

Robocast, ROBOt and sensors integration for Computer Assisted Surgery and Therapy, Dec. 31, 2010.

United States Army Research Laboratory: A Review and Meta Analysis of Vibrotactile and Visual Information Displays, Elliott et al, ARL-TR-4955, Sep. 2009.

Chun Kr et al. J Cardiovasc Electrophysiol. 2009; 20(11)1203-1210.

Sarabanda AV et al. JACC 2005;46(10):1902-1912.

Chiba S et al. Electroactive Polymer "Artificial Muscle" Operable in Ultra-High Hydrostatic Pressure Environment. IEEE Sensors Jounral, vol. 11, No. 1, Jan. 2011, p. 3.

Wu J et al. Proc. IMechE vol. 220 Part D: Automobile Engineering. p. 313, 2006.

Leitmann G. Applied Mathematics and Computation 1995 70: 247-259.

"Cellular Level Biocompatibility and Biosafety of ZnO Nanowires" Zhou Li, Rusen Yang, Min Yu, Fan Bai, Cheng Li and Zhong Lin Wang, J. Phys. Chem. C, 112 (2009) 20114-20117.

(56) References Cited

OTHER PUBLICATIONS

"Piezoelectric-Potential-Controlled Polarity-Reversible Schottky Diodes and Switches of ZnO Wires",Jun Zhou, Peng Fei,Yudong Gu, Wenjie Mai, Yifan Gao, Rusen Yang, Gang Bao, and Z.L. Wang, Nano Letters.,2008.(8),11. 3973-3977.

"Elastic Properties and Buckling of Silicon Nanowires",Cheng-Lun Hsin, Wenjie Mai, Yudong Gu, Yifan Gao, Chi-Te Huang, Yuzi Liu, Lih-Juann Chen,and Z.L. Wang, Advanced Materials.,2008 (20) 20, 3919-3923.

"Flexible Piezotronic Strain Sensor", J. Zhou, Y.D. Gu, P. Fei, W.J. Mai, Y.F. Gao, R.S.Yang, G. Bao and Z.L. Wang Nano Letters, 2008, 8(9),3035-3040.

"Mechanical-Electrical Triggers and Sensors Using Piezoelectric Micowires/Nanowires", J. Zhou, P. Fei, Y.F. Gao,Y.D. Gu, J. Liu, G. Bao and Z.L. Wang Nano Letters, 2008, 8(9), 2725-2730.

"Fabrication of ZnO Nanowire Devices via Selective Electrodeposition",Min Zhang, Zhaoying Zhou,Xing Yang, Xiongying Ye, and Zhong Lin Wang. Electrochemical and Soild-State Letters,11(9) D69-D71 (2008).

Electrostatic Potential in a Bent Piezoelectric Nanowire. The Fundamental Theory of Nanogenerator and Nanopiezotronics,Y.F. Gao and Z.L. Wang Nano Lett., 7 (2007) 2499-2505.

The new field of nanopiezotronics, Z.L. Wang, Materials Today, 10 (2007) 20-28.

Nanowire Piezoelectric Nanogenerators on Plastic Substrates as Flexible Power Sources for Nanodevices, P.G. Gao, J.H. Song, J. Liu and Z.L. Wang Adv. Mater., 19 (2007) 67-72.

Piezoelectric Nanogenerators Based on Zinc Oxide Nanowire Arrays, Z.L. Wang and J.H. Song Science, Apr. 14, 2006: 242-246.

"Pattern and Feature Designed Growth of ZnO Nanowire Arrays for Vertical Devices", J. H. He, J. H. Hsu, C. H. Wang, H. N. Lin, L. J. Chen and Z. L. Wang, J. Phys. Chem. B, 110 (2006) 50-5.

Kim MH et al. Circ Cardiovasc Qual Outcomes 2011; D01:10.1161/CIRCOUTCOMES.110.951865; AHA.

NEJM 2002; 347: 1825-1833.

Dagres N. et al. J Cardiovasc Electrophys Sep. 2009; 20(9): 1014-1019.

Dong, J et al, J Cardiovasc Electrophysiol, vol. 16, pp. 845-852, Aug. 2005.

J Am Coll Cardiol, 2006; 47:2498-2503, doi:10.1016/j.jacc.2006.02.050.

Yuen, S. et al, Robotic Tissue Tracking for Beating Heart Mitral Valve Surgery, Medical Image Analysis, p. 1-11, Jun. 14, 2010.

Yuen, S. et al, Force Tracking with Feed-Forward Motion Estimation for Beating Heart Surgery, IEEE Transactions on Robotics, vol. 26, No. 5, Oct. 2010, p. 888-896.

Yuen, S. et al, Robotic Motion Compensation for Beating Heart Intracardiac Surgery, The International Journal of Robotics Research, p. 2-18, 2009.

Zorcolo, A. et al, Catheter Insertion Simulation with Combined Visual and Haptic Feedback, 1999.

Haruta, M et al., Development of Remote-Type Haptic Catheter Sensor System using Piezoelectric Transducer, Extended Summary, p. 5, 2007.

Bethea, B. et al., Application of Haptic Feedback to Robotic Surgery, J Laparoendosc Adv Surg Tech A. Jun. 2004; 14(3): 191-195.

Ouellette, Jennifer, Smart Fluids Move into the Marketplace, The Industrial Physicist, Dec. 2003/Jan. 2004, p. 14-17.

Patel, Nikunj Manubhai, Design of Haptic Force Feedback for Catheter Insertion Mechanism, Dec. 2006.

Pare, Michel; Joseph E. Mazurkiewicz, Allan M. Smith, and Frank L. Rice (Sep. 15, 2001). "The Meissner Corpuscle Revised: A Multiafferented Mechanoreceptor with Nociceptor Immunochemical Properties". The Journal of Neuroscience, Sep. 15, 2001, 21(18): 7836-7246.

Howe, E., The Plymouth Student Scientist, 2009, 2, (1), 90-107.

Savazzi, S. et al., Interhemispheric transfer following callosotomy in humans: Role of the superior colliculus, Neuropsychologia 45 (2007) 2417-2427.

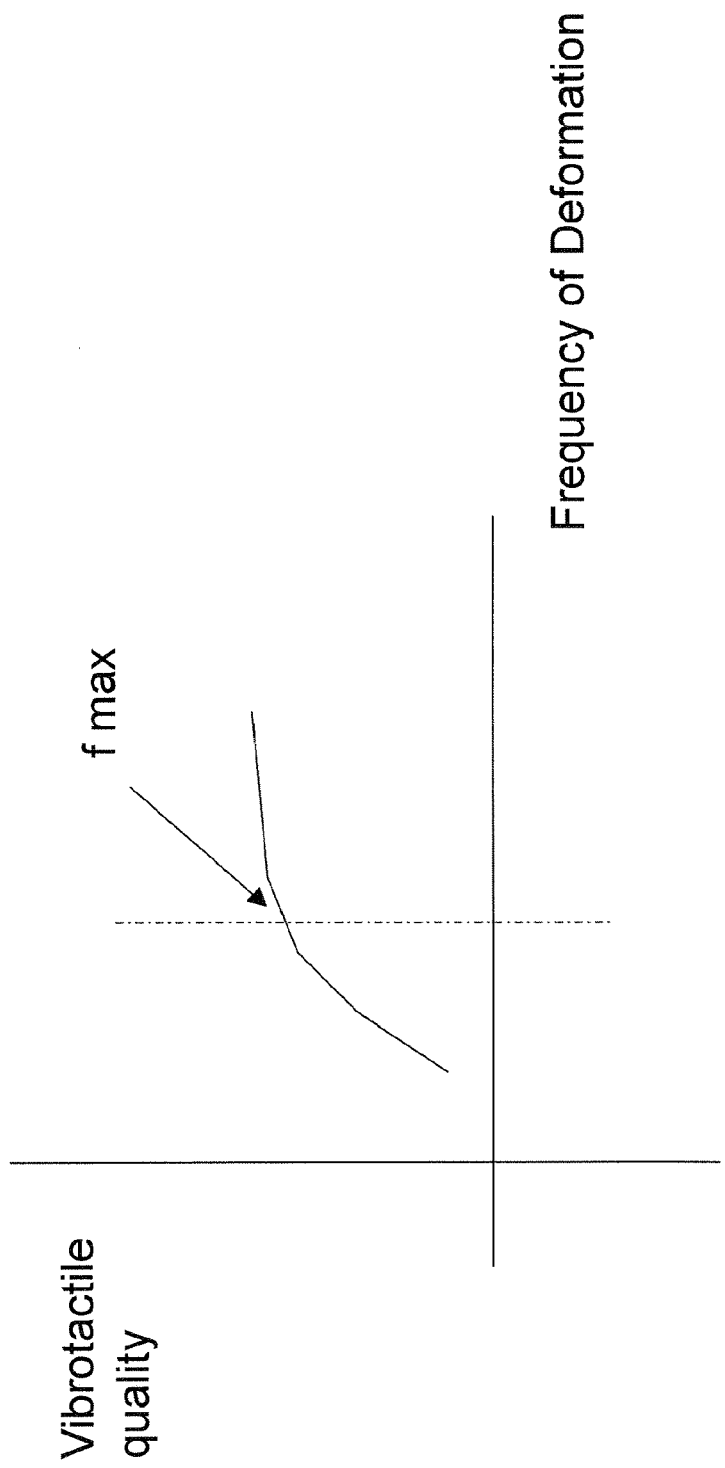

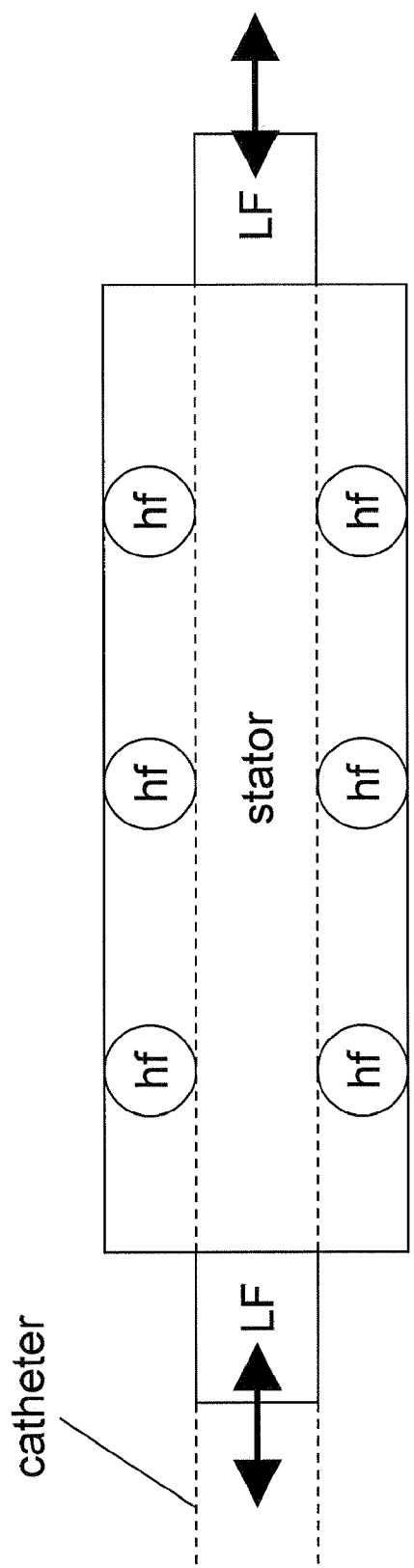

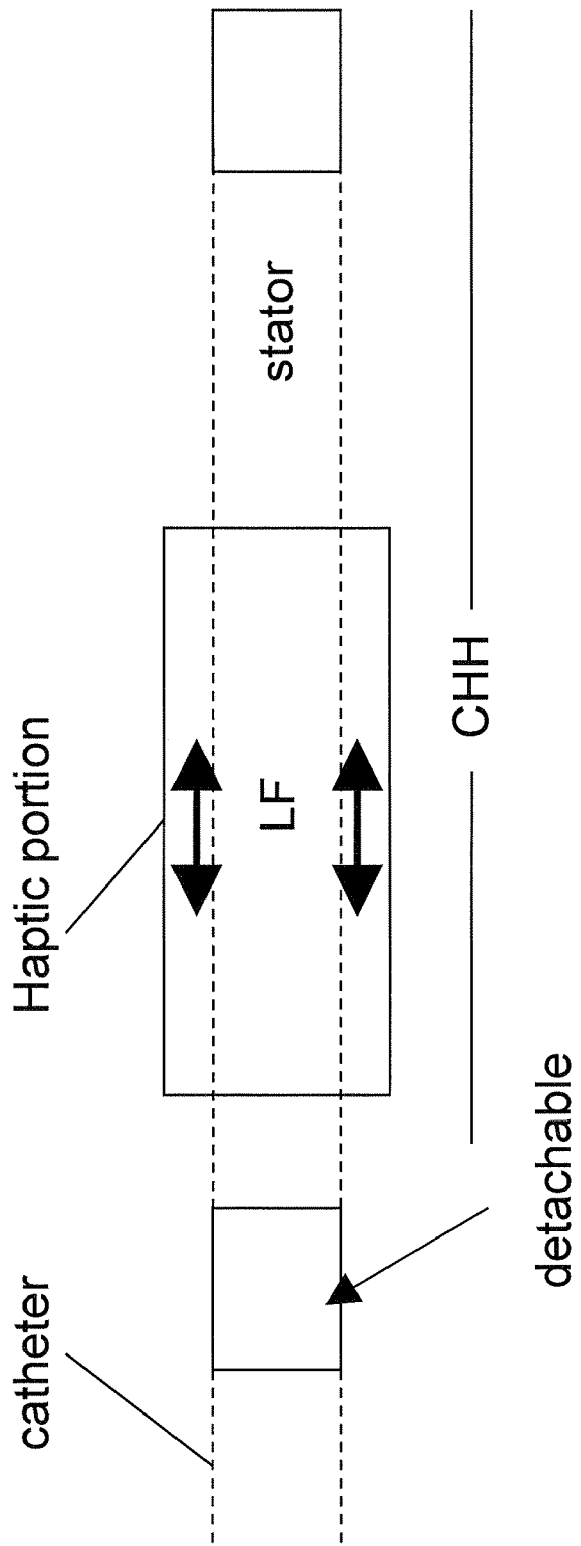

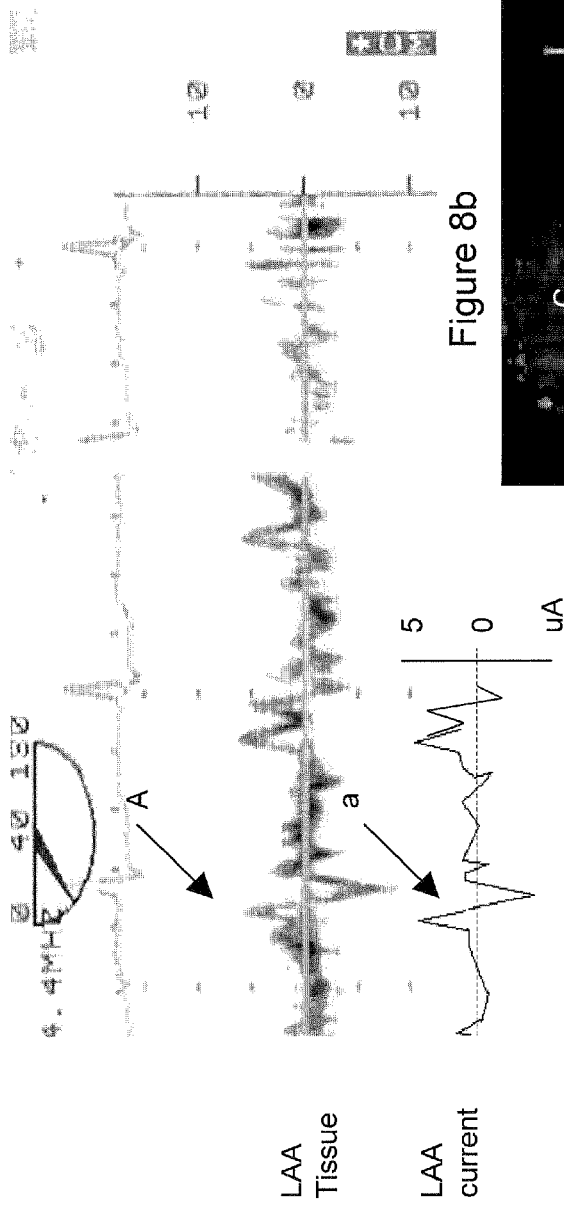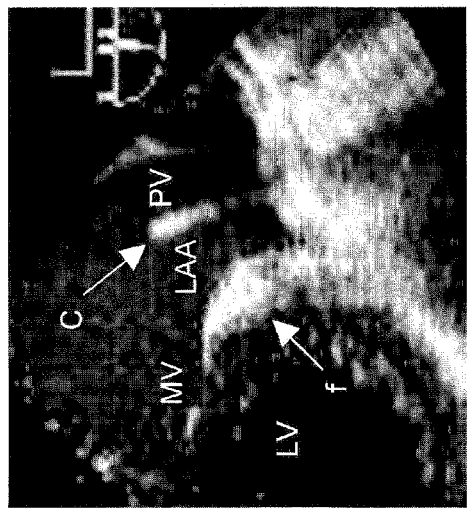
FIGURE 8a
Figure 8b
LA – left atrium
LAA – left atrial appendage
MV – mitral valve
LV – left ventricle
PV – left upper pulmonary vein
C – common wall
f – free wall

CARDIOVASCULAR HAPTIC HANDLE SYSTEM

RELATED APPLICATIONS

I. This application is a continuation of U.S. patent application Ser. No. 13/448,879, filed Apr. 17, 2012, pending, published as US20120265083A1, which is a continuation of U.S. patent application Ser. No. 12/836,636, filed Jul. 15, 2010, now abandoned, published as US2010/0312129A1, which is a continuation-in-part of U.S. patent application Ser. No. 11/686,602, filed Mar. 15, 2007, now U.S. Pat. No. 7,963,925, which is a continuation of U.S. patent application Ser. No. 11/584,465, filed Oct. 20, 2006, now abandoned, which is a continuation-in-part of U.S. patent application Ser. No. 11/334,935, filed Jan. 19, 2006, now abandoned, published as US2006/0167529A1, which claims the benefit of U.S. Provisional Application No. 60/660,101 filed Mar. 9, 2005, and U.S. Provisional Application 60/647,102 filed Jan. 26, 2005, and II. This application is a continuation of U.S. patent application Ser. No. 13/448,879, filed Apr. 17, 2012, pending, published as US20120265083A1, which is a continuation of U.S. patent application Ser. No. 12/836,636, filed Jul. 15, 2010, now abandoned, published as US2010/0312129A1, in which:

(a) U.S. patent application Ser. No. 12/836,636 is also a continuation-in-part of U.S. patent application Ser. No. 12/245,058, filed Oct. 3, 2008, now abandoned, published as US2009/0030332A1, (b) U.S. patent application Ser. No. 12/836,636 is also a continuation-in-part of U.S. patent application Ser. No. 11/848,346, filed Aug. 31, 2007, now abandoned, which is a continuation-in-part of U.S. patent application Ser. No. 11/771,233, filed Jun. 29, 2007, now abandoned, which is a continuation-in-part of U.S. patent application Ser. No. 11/746,752, filed May 10, 2007, now abandoned, (c) U.S. patent application Ser. No. 12/836,636 is also a continuation-in-part of U.S. patent application Ser. No. 11/848,346, filed Aug. 31, 2007, now abandoned, which is also a continuation-in-part of U.S. patent application Ser. No. 11/746,752, filed May 10, 2007, now abandoned, (d) U.S. patent application Ser. No. 12/836,636 is also a continuation-in-part of U.S. patent application Ser. No. 11/848,346, filed Aug. 31, 2007, now abandoned, which is also a divisional of U.S. patent application Ser. No. 11/686,602 now U.S. Pat. No. 7,963,925, which is a continuation of U.S. patent application Ser. No. 11/584,465, filed Oct. 20, 2006, now abandoned, each of which is a continuation-in-part of U.S. patent application Ser. No. 11/334,935, filed Jan. 19, 2006, now abandoned, published as US2006/0167529A1, which claims the benefit of U.S. Provisional Application No. 60/660,101 filed Mar. 9, 2005, and U.S. Provisional Application 60/647,102 filed Jan. 26, 2005, and III. This application is a continuation of U.S. patent application Ser. No. 13/448,879, filed Apr. 17, 2012, pending, published as US20120265083A1, which is a continuation of U.S. patent application Ser. No. 12/836,636, filed Jul. 15, 2010, now abandoned, published as US2010/0312129A1, which is a continuation-in-part of U.S. patent application Ser. No. 11/848,346, filed Aug. 31, 2007, now abandoned, which is a continuation-in-part of U.S. patent application Ser. No. 11/771,233, filed Jun. 29, 2007, now abandoned, which is a continuation-in-part of U.S. patent application Ser. No. 11/746,752, filed May 10, 2007, now abandoned, which also claims the benefit of U.S. Provisional Application No. 60/855,820, filed Nov. 1, 2006, and IV. This application is a continuation of U.S. patent application Ser. No. 13/448,879, filed Apr. 17, 2012, pending, published as US20120265083A1, which is a continuation of U.S. patent application Ser. No. 12/836,636, filed Jul. 15, 2010, now abandoned, published as US2010/0312129A1, which is a continuation-in-part of U.S. patent application Ser. No. 11/848,346, filed Aug. 31, 2007, now abandoned, which is also a continuation-in-part of U.S. patent application Ser. No. 11/746,752 filed May 10, 2007, now abandoned, which also claims the benefit of U.S. Provisional Application No. 60/855,820, filed Nov. 1, 2006, and V. This application is a continuation of U.S. patent application Ser. No. 13/448,879, filed Apr. 17, 2012, pending, published as US20120265083A1, which is a continuation of U.S. patent application Ser. No. 12/836,636, filed Jul. 15, 2010, now abandoned, published as US2010/0312129A1, which claims the benefit of U.S. Provisional Application No. 61/270,924, filed Jul. 15, 2009, and U.S. Provisional Application 61/341,129, filed Mar. 27, 2010, and U.S. Provisional Application 61/396,575, filed May 29, 2010, all of which are incorporated herein by reference in their entireties.

BACKGROUND OF THE INVENTION

1. Field of the Invention

This invention relates to a hand-held haptic control system with tactile force feedback that acquires dynamic cardiac mechanical data as to generate multidimensional tactile simulations of the intra-cardiac environment in real time via a hand held Cardiovascular Haptic Handle (CHH) providing physiologic information in form of a tactual representation in real time. The CHH system eliminates the effects of a catheter's dampening properties, the attenuation effects of intervening tissues and the affect of the operator's gross motions on an inserted catheter's ability to provide the operator with a tactual representation of cardiac tissue motion and the effects of catheter—tissue contact. Though the system can function in conjunction with visual displays, it can provide mechanical and anatomical information with a haptic representation and replace the need for a visual display.

2. Description of Prior Art

Medical catheters and sheaths are generally tubular shaped and of a sufficiently small diameter to be inserted into a patient's body through a small incision, puncture or a natural opening. Such catheters can be used to deploy inner catheters, cardiac leads, electrodes, deliver contrast (e.g. radiopaque dye) or ablative energy in form of electromagnetic energy (e.g. current, radiofrequency energy, light) and are flexible as described by Brock et al in U.S. patent application Ser. No. 12/023,685. One example is lead extraction systems that implement an excimer laser. Unfortunately, as conventionally designed catheters course through a patient's tissues and vasculature the operator looses his or her ability to appreciate the forces restricting catheter motion secondary to attenuation and frictional effects and due to the compliant nature of the inserted catheters.

Catheters for performing coronary/peripheral angiography and vascular interventions are well understood by those experienced in the art. More recently, catheters have been designed for engaging the coronary sinus and positioning pacing leads about the left ventricle for cardiac resynchronization therapy which is often difficult and time consuming requiring large amounts of radiation exposure. These catheters can also dissect vessels and intracardiac structures leading to cardiovascular collapse. Unfortunately, the operator can not appreciate the dynamic characteristics of contacted tissue or the forces along the distal portion of these catheters and mainly relies on radiographic images during catheter manipulation (e.g. fluoroscopy). These images are two dimensional and necessitate exposure to radiation. Tactile feedback systems incorporated into the design of these catheters would reduce complication rates, expedite procedures and minimize radiation exposure to the operator and patient alike and most importantly, provide insights into cardiac tissue mechanics.

Electrograms have been demonstrated to be poor predictors of electrode-tissue contact for ablation procedures (see Ikeda A. et al. Electrogram Parameters (Injury current, amplitude, dV/dt) and Impedance are poor predictors of electrode-tissue contact force (see Electrode-Tissue Contact Force for Radiofrequency Ablation. Heart Rhythm Society, May 2008, Abstract 4570, P05-41).

The phasic nature of the contracting heart and respirations affects lesion characteristics from ablative energy because of intermittent contact and variations in applied force at the electrode-tissue interface (Shah D C et al. Area under the real-time contact force curve (force-time integral) predicts radiofrequency lesion size in an in vitro contractile model. J Cardiovac Electrophysiol, 2010, pp 1-6). Real-time tactile force-feedback via the Haptic Handle will ensure safe and effective delivery of therapy without a need for the operator to look away from the visual/fluoroscopic image of the heart and obviates a need to look at a separate force graphic display during critical time frames. The CHH will complement technologies that provide force information (available e.g. from Enclosense Tacticath of Geneva Switzerland, Hansen Medical of Mountainview, Calif.) and improve outcome with minimal additional expense, obviate the need for expensive navigational systems and reduce fluoroscopic exposure. It will also enable the operator to more deeply sedate patients during their procedures as verbal feedback of discomfort during delivery of ablation energy will not be necessary.

A variety of devices can be used as a haptic display including but not limited to programmable keyboards, augmented mice, trackballs, joysticks, multi-dimensional point and probe-based interactions, exoskeletons, vibro-tactor arrays, gloves, magnetic levitation, and isometric devices (Burdea, G C. Force and Touch Feedback for Virtual Reality. New York: Wiley Interscience, 1996). These systems are used for virtual simulations or for evaluation of non-moving, static structures. There remains a need for haptic representation of moving biological tissue.

Mottola et al (U.S. Pat. No. 6,059,759) describes an infusion catheter system with an occluding wire that generates vibrations when the wire protrudes along a ridge notifying the operator that the wire extends beyond the confines of the inserted catheter. This does not provide the operator with information about the mechanics of cardiac motion/deformation or the effect of the catheter on cardiac mechanics.

Wallace D, et al has developed a robotic catheter manipulator that includes at least one force sensor for measuring the force applied to the working catheter by a ditherer during operation (U.S. patent applications publications nos. 20070233044, 20070197939). Force measurements are estimated and displayed to the physician via a monitor or display. In Wallace's application, an alarm signal can notify the operator that too high a force is applied via an audio, video or haptic signal, though there is no tactile appreciation or simulation of tissue mechanics/motion present at the distal portion of the catheter. Such a design is found in ablation catheters manufactured by Hansen Medical Inc., Mountainview, Calif.

No current technology provides the operator with a dynamic mechanical simulation of the heart, surrounding vasculature or the effect of an inserted instrument on cardiovascular tissue deformation and motion. The addition of tactile force feedback to commonly used catheter manipulators will provide an operator with a unique ability to sense the physical action of an inserted catheter on a rapidly moving biological structure while controlling fine motion of the catheter's distal aspect and acquiring physiologically significant data about cardiac function.

References—to be Listed Separately in an IDS.

SUMMARY OF THE INVENTION

It is clear to the inventor that there is a great need in the art for systems that provide surgeons using catheters with various tactile information during a procedure, especially cardiac diagnostic procedures where normal and pathological physiologic information can be acquired as to assist in delivery of appropriate therapies. The present invention pertains to a system in which catheters or external sensing systems are provided with haptic rendering of cardiac tissue motion characteristics.

Though haptic rendering through any means (including teleoperation) is within the scope and spirit of this invention, the preferred mode for real-time rendering is via a volumetric Haptic Handle that most closely simulates handles that are part of conventionally used dexterous intravascular catheters familiar to cardiologists, surgeons and electrophysiologists who currently perform invasive cardiac procedures and lead extraction procedures. Transducers provide passive simulation of cardiac tissue motion and also can be coupled with active elements that direct the motion and location of multiple segments along an inserted catheter.

Various types of motors can be provided to implement rendering tactile force and vibrotactile feedback including but not limited to longitudinal/linear, rotary, ultrasonic, piezoelectric, normally locked, normally free motors, etc. as known by those experienced in the art (e.g. U.S. Pat. Nos. 3,184,842, 4,019,073, 4,210,837).

Miniaturized sensors such as piezoelectric sensors or accelerometers are used to acquire intra-cardiac data representative of myocardial wall motion. The sensors produce signals in response to the motion of the ventricular wall locations that relate to mechanical tissue characteristics during the cardiac cycle but do not provide a tactile simulation of dynamic cardiac properties in real time.

Other types of sensors are used that may be based on electromagnetic systems to gather information about tissue mechanics. For example, the sensors described by Aeby and Leo to sense tri-axial forces incorporate optical fibers to generate variable intensities of light as a function of deformation (see U.S. patent application publication number 20080009759). These systems provide the operator with measurements of contact force at the catheter's distal end and three dimensional anatomic localization data. Externally located magnetic and electromagnetic fields found in three dimensional navigational systems are known that provide cardiac anatomic information (e.g EnSite NavX system (St. Jude Medical, Austin, Tex.) but do not communicate dynamic cardiac tissue mechanical information to the operator nor provide tactile feedback.

BRIEF DESCRIPTION OF THE DRAWINGS

FIG. 6 shows how a maximal frequency, f max, is reached while the actual frequency of deformation of the sensor (abscissa) increases but is not accurately represented in the haptic display (ordinate).

FIG. 7b illustrates multiple high frequency rotary motors and a low frequency longitudinal motor (stator) within a Cardiovascular Haptic Handle, CHH.

FIG. 7c illustrates an alternative embodiment for a Cardiovascular Haptic Handle.

FIG. 8a illustrates how the fine, high frequency motion of the fibrillating LAA generates a proportionate amount of current as a function of time which is translated into a similar quality motion in the haptic display.

FIG. 8b is a transesophageal image illustrating the proximity of the left upper pulmonary vein (PV) to the LAA and associated structures.

DETAILED DESCRIPTION OF THE INVENTION

Data Acquisition

Motion Sensors

In one mode of this invention, temporary or permanently implanted cardiovascular instrumentation (e.g. cardiac catheters or implanted pacemaker/defibrillator leads, respectively) is equipped with transducers that acquire sensor signals from within the cardiac tissues and surrounding vasculature. By way of example, a piezoelectric sensor acquires information related to the motion of the contacted cardiac tissues and flow characteristics of intra-cardiac blood (e.g. turbulence, laminarity). The motion and/or deformation of the sensor are directly proportionate to that of the neighboring tissues or fluid flow. The amount of piezoelectric voltage generated will bear a relationship (i.e. linear, exponential) to sensor motion/deformation. Physiologic indices that can be derived from these measurements include but are not limited degree of displacement, torque, frequency of motion (can be along specific vectors), anatomic localization, sensor orientation, characteristics of blood flow, force information (also described in the inventor's co-pending patent application Ser. No. 12/245,058, incorporated herein by reference). These indices are applied to provide a haptic control system as a means for navigating about the vasculature and heart, performing therapeutic procedures and collecting novel physiologic information.

In one mode of the invention, piezoelectric sensors (e.g. deformation or acoustic sensor) detect properties of tissue displacement including the natural motion/deformation of the vasculature and cardiac structures, and the effect of catheter manipulation and/or displacement caused by an inserted catheter. Such sensors can be constructed of conventional piezoelectric material such as PZT (lead, zirconate, titanate) or other material/composite. They can be located in one or more locations along the inserted instrument. For catheters used for ablation of arrhythmia, the location is such that interference with the sensor secondary to ablative energy does not occur and sensor integrity is not affected.

Figure 1:
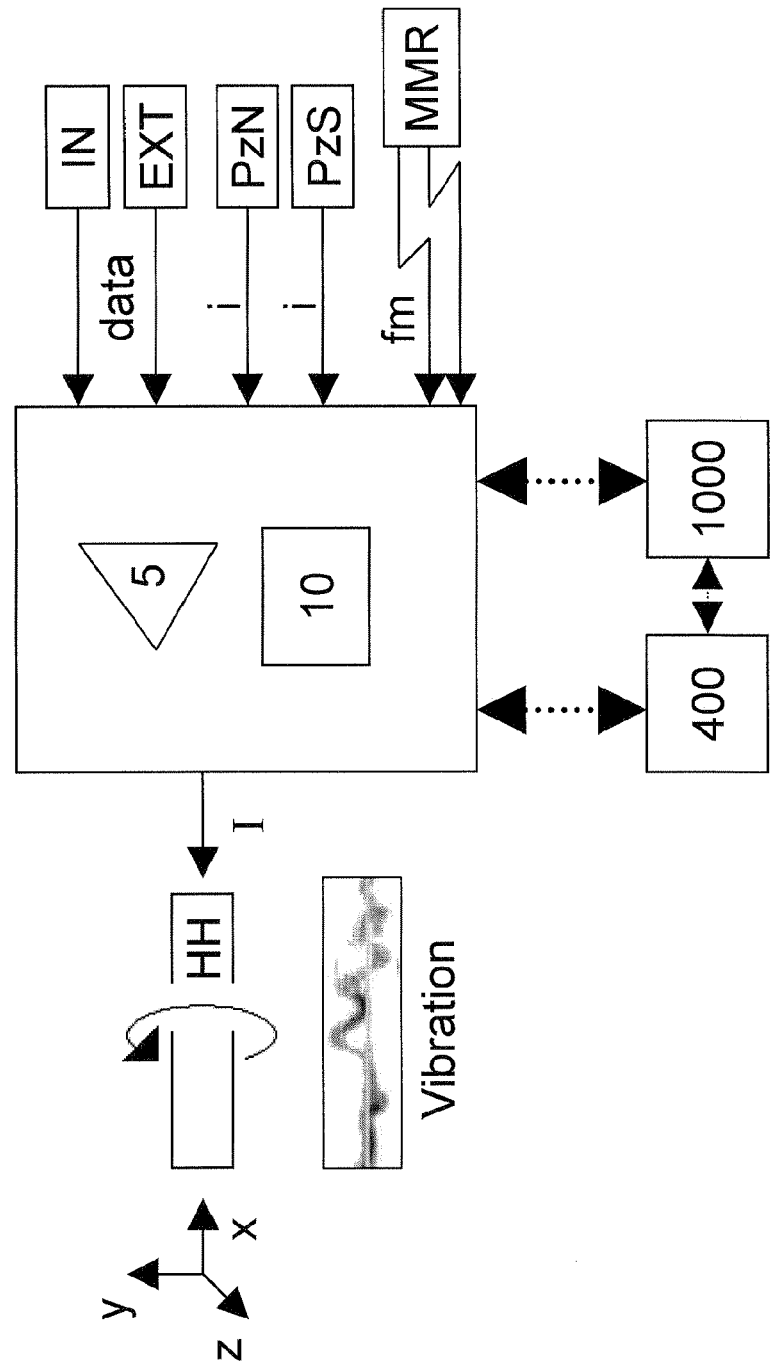
FIG. 1 shows a block diagram for handling information in accordance with this invention.

FIG. 1 shows a block diagram for handling information in accordance with this invention; sensors (e.g piezoelectric) detect multidimensional motion. Sensors can be conventional piezoelectric, PzS, or nanosensors, PzN, constructed using nanotechnology. Voltage output by the PzS is proportionate to sensor motion/deformation. The resulting electrical signal, i, is provided through a conductor (conventional or nanoconductors) can be either amplified at 5 and/or input into a controller/processor, 10, that delivers waveforms, (for example, current waveforms I), to a Haptic Handle, HH, which simulates cardiac tissue motion and the affect of omni-directional catheter motion and deformation on such tissue motion to the operator. The controller is preferably capable of high level haptic rendering as described in detail below. The controller/processor, 10, has bidirectional communication with processing centers 400 (peripherally located) and 1000 (centrally located), as well as, conventional diagnostic imaging equipment, 700, as described in the parent application. In one embodiment, 10, serves to perform haptic rendering to sensed signals and deliver commands to the CHH and from the CHH to the inserted instrument(s).

Acquisition of motion information using piezoelectric sensors and piezoelectric nanosensors (also described in inventor's co-pending patent application Ser. No. 12/245,058 incorporated herein by reference) enables high fidelity reproduction of sensed signals in the CHH. In one embodiment of the invention, the analog data acquired by the sensor is in form of an electrical signal corresponding to the motion/deformation of PzS. This information includes one or more characteristics of the motion/deformation of PzS, such as frequency, vector and degree of displacement. Sensors that can be used for this purpose include sensors made of a piezoelectric material, accelerometers, microsonometers and other similar sensors known to persons skilled in the art. Alternatively or additionally, the input data can be acquired by an external or extrinsic means (EXT in FIG. 1) as discussed more fully below.

Figure 2:
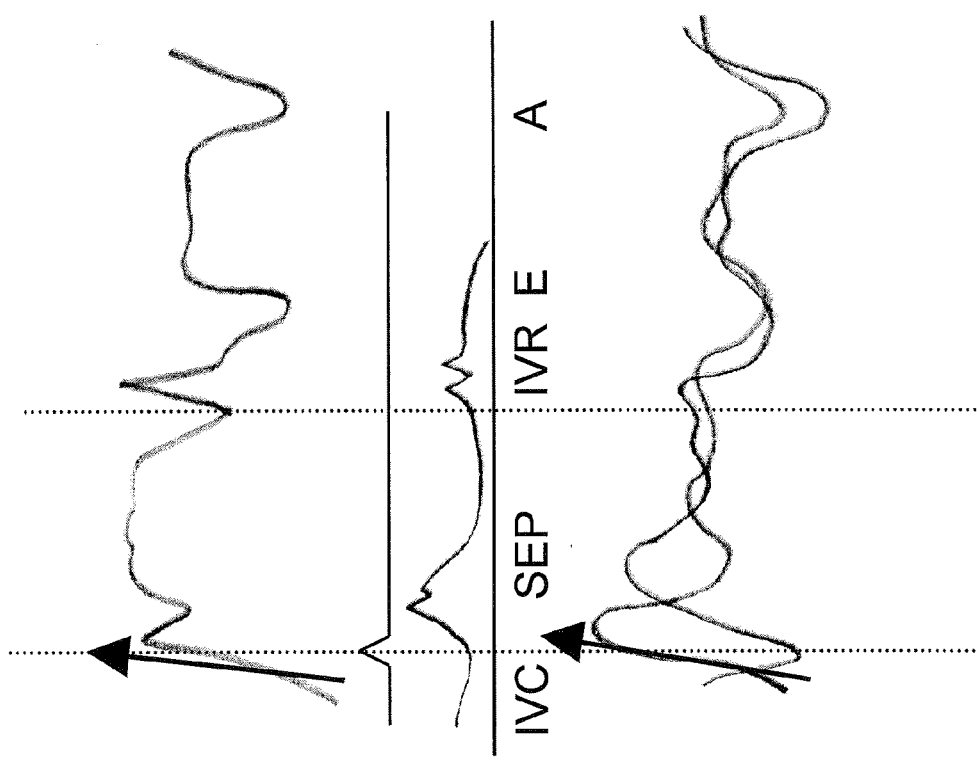
FIG. 2 illustrates analogous signals of cardiac motion obtained with intra-cardiac sensors (middle) and tissue Doppler echocardiography (top—longitudinal motion, bottom—rotational motion). Sensors deployed in different locations and with different orientations along an inserted catheter will gather motion information along different vectors.

Referring to FIG. 2—middle, we see a current time graph illustrative of lead or catheter motion at the level of the atria-ventricular valvular annulus (along the plane of the coronary sinus) detected by an LV lead or coronary sinus catheter-based accelerometer(s). The lead has PzS incorporated within its structure. Optimally, the lead/catheter remain isodiametric and in a preferred mode of the invention, PzS is constructed with nanotechnology (e.g. carbon nanotube transducers), though other sensors can be used as well, as discussed. On the bottom of FIG. 2 is a rotational displacement time graph depicting left ventricular torsion as determined by echocardiographic speckle tracking or other imaging technique. On top is a myocardial tissue velocity time graph (detected with ultrasonic tissue Doppler imaging). One heart beat is depicted. Current peaks (middle) are noted at times of maximal rotational velocity and displacement during isovolumic contraction (IVC) and isovolumic relaxation (IVR). Less current flow is noted during the systolic ejection phase and diastolic time frames (E=passive filling and A=active filling). Sensor technology, signal processing as detailed herein and haptic rendering are required in order for multiple cardiac motion characteristics (e.g. secondary to LV rotation and atrial flutter) to be tactually appreciated simultaneously (See Schecter et al. The Effects of Atrial Flutter on Left Ventricular Rotation: A Tissue Doppler Study. Heart Rhythm Society 2005; 2(1S): S134).

Figure 3:
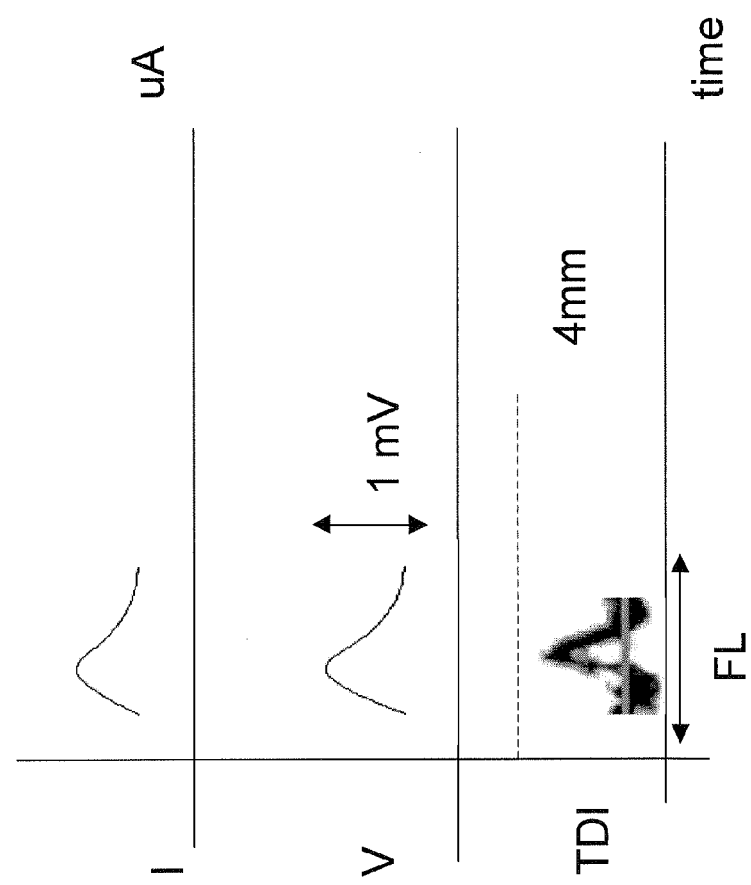
FIG. 3 depicts tissue Doppler motion, TDI, bottom and current waveform from a piezoelectric sensor (top) and voltage waveform (middle) from motion detected within the left atrial appendage, LAA, in a patient with atrial flutter.

FIG. 3 illustrates how the voltage generated at the level of the sensor, V, and current, I, conducted to 5 and 10 are proportionate to the degree of displacement of the PzS. Ultrasonic tissue Doppler imaging (TDI) measurements of displacement correlate with V and I for one cycle of atrial flutter sensed with PzS (intrinsically) and extrinsically with echocardiography equipment. In FIG. 3, one flutter cycle lasting approximately 200 milliseconds (double arrows along abscissa) is depicted. Extrinsic sensing with ultrasound serves to calibrate novel intrinsic sensors and help define the physiological significance of the newly acquired tactual metric of motion as described in the inventor's co-pending patent application Ser. No. 11/584,465, incorporated herein for reference.

The implanted sensors are preferably made using microfabrication techniques to will facilitate the system's ability to reproduce vector of motion, such that the haptic display can generate a tactual representation of more than one type or vector of motion in more than one format (e.g. rotational and longitudinal velocity, acceleration, displacement). Such motion is detected by one or more sensors and can be simultaneously or independently simulated in the Haptic Handle depending on operator preference. Devices, including self-ampifying nanogenerators can be used for this purpose as are disclosed by Qin Y, Wang X, Wang Z L. Microfibre-nanowire hybrid structure for energy scavenging. Nature. Vol 451, Feb. 14, 2008. 809-813.

Figure 4B:
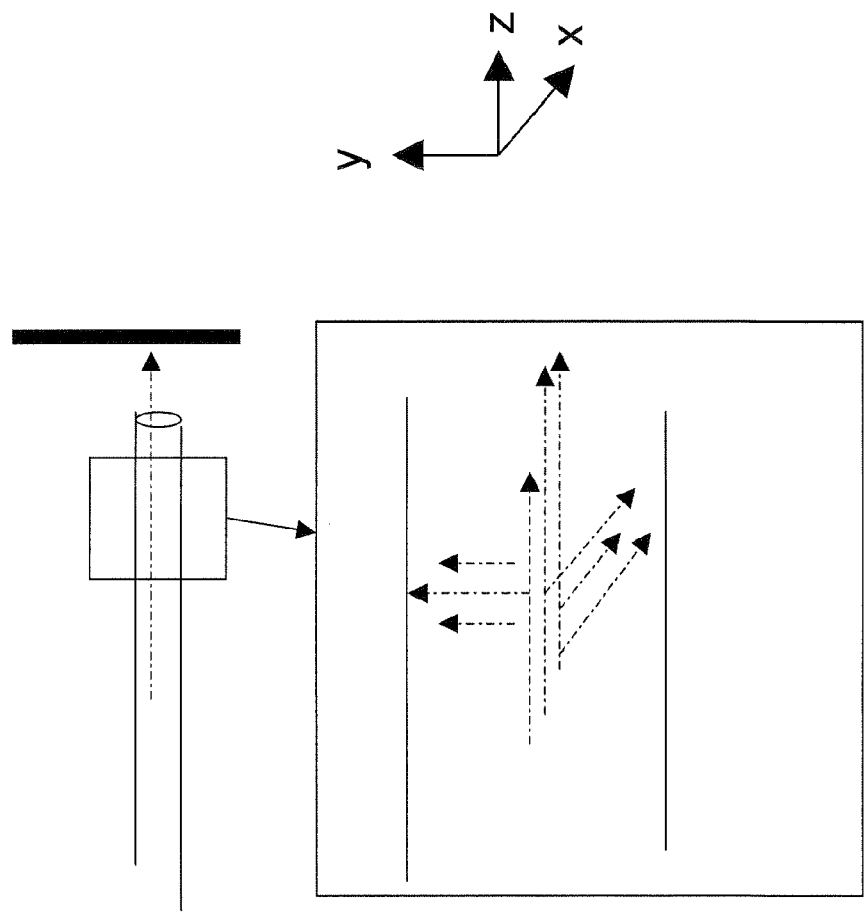
FIG. 4b is a depiction of multiple nanosensors deployed in three dimensions in the distal portion of an intra-cardiac catheter.
Figure 4A:
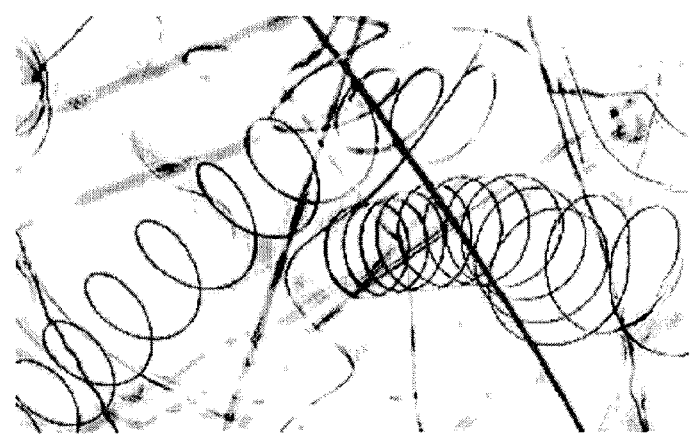
FIG. 4a is an electron micrograph of helical nanosprings
Figure 4C:
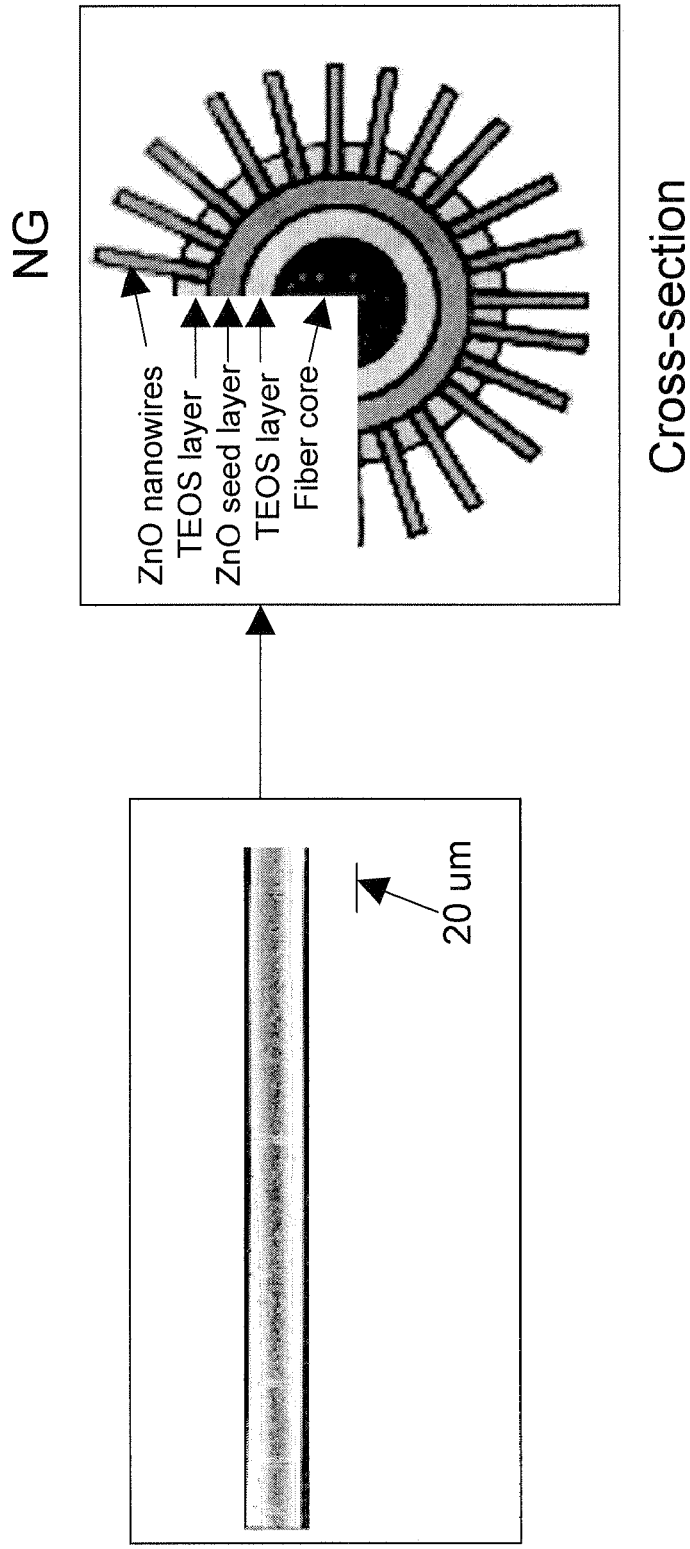
FIG. 4c left is an electron micrograph of an individual ZnO nanowire and 4c—right illustrates how nanowires are radially positioned about a Kevlar fiber core mechanically reinforced with layers of TEOS (see text for details) create a nanogenerators (NG).

The nanosprings and nanogenerators illustrated in FIGS. 4a and 4c, respectively, provide a more accurate signal than conventional accelerometers, and generate a relatively large amount of current relative to the degree of deformation improving signal to noise ratio also described in inventor's co-pending patent application Ser. No. 12/245,058 incorporated herein by reference.

Integration and differentiation can be performed on the acquired data and velocity, acceleration and/or displacement is presented within the CHH based on the preference of the operator. For the purposes of clarity, a one degree of freedom (1-DOF) tactual displacement metric is described, though velocity and acceleration properties can be preserved in the final haptic representation as well. If preferred, the effect of the tissue motion upon the catheter, as well as, the effect of other forces (e.g. generated by the operator) on the catheter's motion can be appreciated at the haptic end or subtracted from the final tactual representation. Preferably, multiple sensors and sensor types are positioned at specific locations as to gather specific motion characteristics (at varying frequencies) along the inserted instrument in three dimensions (FIG. 4b). The most distally located sensors will acquire data from contacted tissue while more proximally located sensors will acquire data from catheter motion (e.g. catheter fling) that can be subtracted from the final tactual representation.

When sensors are arranged in three dimensions (FIG. 4c), three dimensional recreation of catheter motion will be possible. Extrinsic navigation systems (e.g. magnetic, impedance-based) can be used to determine the proper frame of reference so that the haptic display is correctly oriented and accurately reproduces the vector of motion in three dimensional space in real time relative to the inserted catheter's and patient's position.

In another embodiment, micromechanical sensor arrays composed of piezoelectric MEMS resonators (MMR in FIG. 1) are used for data acquisition and data transmission occurs wirelessly at gigahertz frequencies (as described by Nguyen, CTC, IEEE Spectrum December 2009). Thus in this embodiment, data is wirelessly transmitted at high frequency to a processor that detects this specific bandwidth and translates the acquired signal to a metric that is tactually communicated in the Haptic Handle.

Regardless of the type of sensor employed the system is capable of extracting and reproducing a wide spectrum of tactile sensations from moving tissue including but not limited to; periodic vibrations (e.g. LAA fibrillating), texture effects (chordae tendinae, LAA ruggae), sensations of enclosure (e.g. intracavitary, within pulmonary vein, coronary sinus), saturation, stiffness (e.g. free wall), thickness (e.g. interatrial septum), spring effect, deadband, inertia, damper effects, constant force, ramp force and friction (e.g. intravascular), simulation of blood flow (laminar and turbulent).

Data Acquisition

Force Sensors

Figure 5:
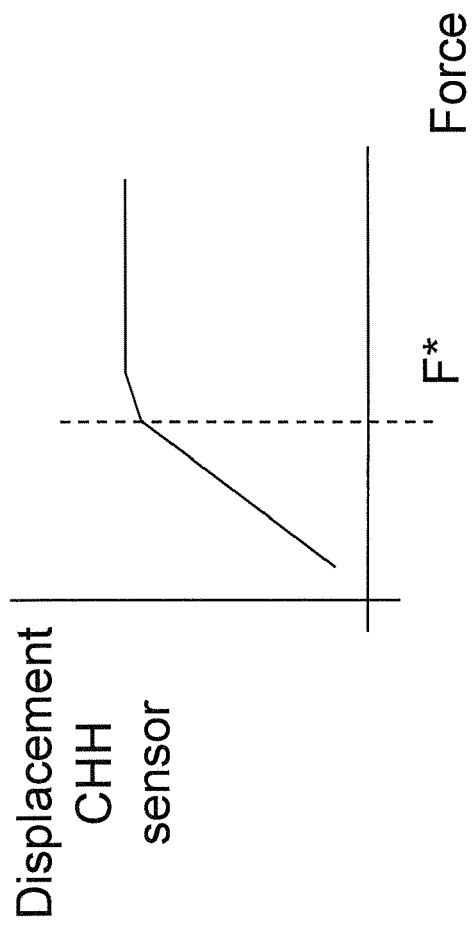
FIG. 5 force information as a function of time can be tactually communicated directly as displacement in the haptic handle such that the force is linearly converted to a tactual metric of displacement with a force proportionate to the sensor force. The relationship may be linear but plateaus at force, F*. The plateau force is dependent on a number of factors including the mechanical properties of the sensor.

The CHH is compatible with force or pressure sensor technology and data acquisition can be made with force/pressure sensors instead of, or in addition to, motion sensors. Force sensors can be in any form including but not limited to fiber optic sensor for resolving the magnitude and direction of force vectors wherein changes in light intensity and/or wavelength of the light transmitted through the an optical element changes as a result of regional strain. Force sensors of this kind are described in as described in Aeby and Leo's patent application publication 20090177095. Acquisition of needed data with pressure sensors can be implemented as well. Force measurements are translated into motion information (e.g. admittance haptic display) and tactually represented in more than one way. By way of example, force information as a function of time can be tactually communicated directly as displacement in the haptic handle such that the force is linearly converted to a tactual metric of displacement (FIG. 5). A Haptic Interface of the admittance type is used to perform this task in one embodiment (see below). When peak force is detected, the handle will reach its peak linear displacement.

In one mode, the processor, 10, converts a force metric to a displacement metric. Assuming a constant sensor mass (Ms) we derive acceleration of the sensor ($a_s$). Thus, sensor force, $F_s = M_s * a_s$. Double integration of $a_s$ will derive displacement, mm.

The Haptic Handle can then displace in three dimensions according to multidimensional force sensor data acquired. Force sensors are more limited in providing the operator with high frequency information than piezoelectric sensors. Referring to FIG. 6, we see a maximal frequency, f max, where the actual frequency of deformation of the sensor (abscissa) increases but is not accurately represented in the haptic display (ordinate) and vibrotactile simulation is suboptimal. Piezoelectric sensors more accurately acquire higher frequency information. In one embodiment, force sensor technology is implemented for representation of gross motion in three dimensions (e.g. low frequency component of hybrid Haptic Handle) and piezoelectric sensors temporally provide motion characteristics in fine detail (e.g. high frequency vibrotactile component of hybrid Haptic Handle). Thus, in a preferred embodiment, a combination of sensors input data to processor, 10, for haptic rendering and optimal coupling. Comparison of analogous data collected with differing intrinsic sensor technologies along with data collected with extrinsic modalities will enable the identification of optimal sensor applications for the creation of the most passive system (e.g. via open connectivity/wireless communication) as described in the inventor's co-pending patent application Ser. No. 11/334,935, incorporated herein for reference.

Data Processing

Extrinsic Navigational Systems

When extrinsic modalities such as navigational systems are used for data acquisition, the transmitted data consists of the three dimensional location of the distal segment(s), (EXT in FIG. 1). Data transmission can occur between the extrinsic system either wirelessly or via conductor(s) and the location information is input for processing into processor, 10, and converted to motion information so that the data is the presented tactually to the operator based on real time anatomic location of one or more portions of the inserted catheter's/instrument's distal end at discrete points in time. Haptic rendering optimizes system transparency, and provides for fluid motion even when a discrete time controller is used for data acquisition (e.g. interpolation). This is discussed in more detail below. An example of a haptic display in this capacity is one that acquires location data and outputs force (impedance display—see below).

Data Processing

Sensor Output

The final sensor data or input data is representative of dynamic cardiovascular tissue motion data combined or not combined with the effect of interactive forces between one or more inserted catheters/instruments on contacted tissue and surrounding fluid. Input data is input to a processor/controller (10) that, in one embodiment, compares the resultant intrinsically acquired motion data with analogous extrinsically acquired data from conventional extra-cardiac imaging modalities (ultrasound, radiation, magnetic, electromagnetic, impedance, electric) such as 3D navigational systems for derivation of a tactual metric that is standardized and calibrated in form of a novel tactile physiologic metric. The processor/controller then outputs the data in real time as tactual simulation of acquired data (e.g. displacement) as is or as a time derivative to the operator via the haptic interface. Displacement, velocity and acceleration/force information at the proximal haptic handle closely simulate the same physical motion characteristics at the distal sensor end in real time providing the user with a good feeling transparent appreciation of intracardiac motion characteristics.

In order to optimize signal fidelity, processor 10 provides amplification and filtering of piezoelectric generated current signals. This can also be done at any point within the system (e.g. distal, central or proximal locations). Processing and amplification that occurs closest to the sensor may optimize signal fidelity but suffers from the drawback of increasing the size and bulk of the inserted instrument/catheter system. In one embodiment, implementation of nanogenerators composed of radially oriented ZnO nanowires, NG, as the active sensor(s) satisfies both the need for a higher output signal and for motion data acquisition (FIG. 4c). Microfabrication techniques provide the necessary miniaturization (Qin Y, Wang X, Wang Z L. Microfibre-nanowire hybrid structure for energy scavenging. Nature. Vol 451, Feb. 14, 2008. 809-813). Use of external sensors (EXT) would circumvent need for signal amplification.

Haptic Handle

Constructs

Real-time cardiac tissue motion/deformation data acquired by one or more sensors in contact with the heart and surrounding structures is communicated to the clinician via a tactile force feedback system within the Haptic Handle. In a simplified embodiment amplifier, 5, is used to deliver signals related to internal characteristics being sensed by the sensor to drive one or more elements within the Haptic Handle, HH (FIG. 1) thereby providing a respective tactile rendering of the corresponding internal characteristics. HH can be contained within conventional handles (e.g. U.S. Pat. No. 6,780,183) used for positioning pacemaker leads, catheters, or intravascular delivery/extraction systems, integrated into ablation catheter systems and the like. The intensity of the tactile feedback is adjustable as some operators may desire a more subtle sensation than other operators especially early on in the learning curve. In a preferred embodiment, specific frequency ranges and haptic characteristics are displayed at different positions and with differing methods along the CHH.

Via the Haptic Handle, the operator will be able to detect when the catheter tip is intracavitary (sense of enclosure), juxtaposed to the IAS (thickness, stiffness, spring), within the LAA (periodic, texture), affected by blood flow at coronary sinus os (intermittent constant force), LA free wall (stiffness, spring, dampen), or near the mitral valve apparatus (vibration, constant force secondary to transmitral blood flow) even with cardiac cycle dependent changes in anatomic structure.

Figure 7A:
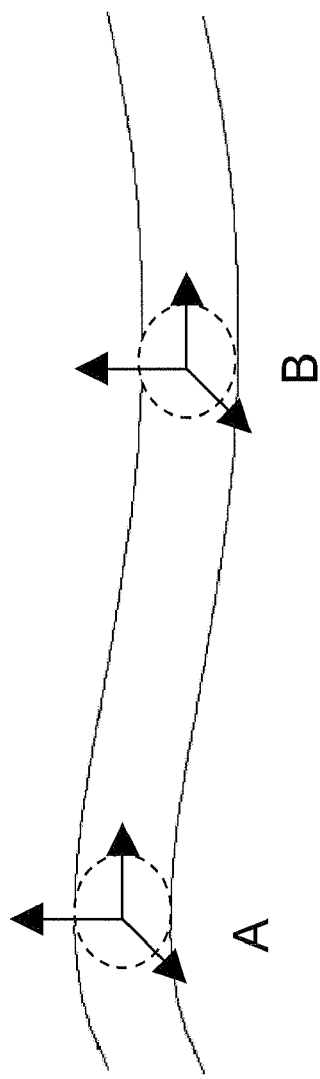
FIG. 7a depicts nodes A and B that are present in a CHH virtual catheter design that shares the properties/construction features of the distal end. Cardiac tissue motion characteristics are acquired via internal and/or external sensors at specific nodes along the inserted catheter/instrument and communicated at multiple joints or nodes (nodes A and B in Figure) along the CHH (virtual coupling). These nodes are present in a simulated version of the catheter which acts as the haptic display.

In one embodiment, torsional/rotational data is acquired with multiple sensors positioned about an inserted instrument/catheter and is simulated with a virtual catheter design. By way of example, a multi-electrode coronary sinus catheter can extract motion information about the basal portion of the heart. This location is ideal as physiologically relevant basal left ventricular rotational information can be acquired. In one mode of the invention, the data is communicated to the operator with a simulated version of the inserted catheter that is held with both hands (virtual catheter). Distal and proximal tissue rotational data is transmitted separately to both hands such that one hand palpates the amplitude and vector of tissue motion along the proximal portion of the catheter and the other from the distal portion. In one embodiment, a virtual catheter can be held and motion information/force along the length of the inserted catheter is palpated by the operator giving a real-time feel of how the distal end is moving at varying pivot points, joints or nodes (FIG. 7a). The action of the operator on the virtual catheter directs the motion of the inserted instrument (virtual coupling) and vice versa.

Haptic Handle

Display Range

The relative dimensions of the cardiac/vascular compartments (CVC) and operating range of the haptic display (HD) can be scaled 1:1 or otherwise (e.g. CVC>HD; CVC<HD). In this fashion, the operator can modify his or her virtual experience/space and be able to continuously appreciate the full range of multi-dimensional motion without system instability. By way of example, maneuvering about a large space (e.g. a 7 cm diameter atrium or between right and left atria) will require a scale downed haptic display range (HD<CVC) as to enable the controller to be implemented comfortably and occupy a reasonable operating volume. When fine motion is required within a confined anatomic space (e.g. about the pulmonary veins, during opposition to cardiac tissue during ablation), an up-scaled haptic display range will be appropriate (HD>CVC). Thus, the operator can reset the haptic display range as needed. Post-processing in processor 10, can be used in order to adjust all the transmitted data (e.g. displacement, velocity, acceleration) once modifications of haptic display range are programmed.

Haptic Handle

Vibratory Tactile Feedback System

In one mode of this invention, the handle accommodates one or more tactile elements in the catheter handle. These elements provide tactile sensations to the hand of the operator. These tactile sensations may be produced by causing the elements to vibrate and/or causing them to be displaced either linearly or rotationally. The vibration of the tactile elements can be accomplished by using for example one or more actuators such as motors rotating weights that are offset from the center of rotation of the motor, though, other tactile/force feedback mechanisms can be utilized to provide varying tactile sensations that can be simultaneously sensed. The vibrations are true reproductions of cardiac tissue vibrations/motion and describe physiologically relevant information to the operator rather than just a warning vibratory signal.

In one mode of the invention, the high frequency motion information is communicated to the operator using more than one haptic display in form of sonomicrometers or speakers that vibrate with the same frequency and displacement as the signals generated from one or more anatomic portions of the heart. The haptic display(s) are positioned about the operative field as to provide the operator with a spatial representation of the location of the inserted sensors in real time. In one embodiment, the frequency range is transposed to be within the audible range of human hearing.

Preferably, simulation of intra-cardiac motion is provided by several tactile elements (driven by individual motors with unbalanced weights as required, or other similar actuators) and housed in the CHH. The shaft(s) of one or more motors positioned with varying directions (e.g. x, y, z axes). Each actuator can receive and reproduce motion characteristics with differing bandwidths and from differing locales along the inserted catheter (e.g. within the respective cardiac chamber, vessel) along three dimensions. By way of example and in one embodiment, the CHH body provides high frequency tactile simulations, the body of the CHH. The shaft reciprocates in a longitudinal direction simulating low frequency cardiac contractile motion. A knob, collar, or other distally located controller at the CNN's distal end (such as Temp-Text knob 204a in FIG. 12) simulates intermediate frequency motion for texture and temperature sensing. Texture characteristics can be simulated using haptic rendering techniques such as delivering variations in frequency and high frequency displacement amplitude. The distal portion of the inserted catheter has a temperature sensor as known by those experienced in the art understand. This temperature sensor delivers readings to controller 10 which then directs Temp-Text knob (204a in FIG. 12) to vibrate at a proportionate frequency and/or amplitude that is indicative varying levels of heat (psychophysical haptic rendering). In one embodiment, the distally located knob or controller is also used to deflect, torque or move one or more portions of the inserted catheter as is well known in the art.

Referring to FIG. 7b we see six high frequency motors HF (or other similar actuators) responsive to high frequency motion sensed in the catheter that provide physiologically relevant vibrotactile motion, a centrally located, low frequency (LF) motor or other actuator responsive to low frequency motion, and a shaft for 1 DOF simulation of cardiac tissue motion that is reproduced in a longitudinal plane. The shaft acts as an actuator to activate a respective tactile element in the handle. As previously described, the tactile element can be a knob, collar or other similar element(s) on the handle. Some existing catheters are equipped with knobs and/or collars and/or triggers used for the manipulation of the catheter (including its tip). In the present invention, the knob or collar etc is coupled to a respective actuator so that they can serve dual functions of manipulating the catheter and providing tactile sensations as discussed. The shaft is stationary relative to the other portions of the handle and in one embodiment its motion is the same as that of the catheter itself (FIG. 7b). Alternatively, longitudinal motion is independent of the catheter and the operator holds a stationary handle (stator or shaft) and a portion of the handle (haptic portion) acts at the tactile element and provides a 1-DOF motion to and fro and can be palpated as to reproduce and provide an appreciation of the cardiac tissue motion at the distal end of the inserted catheter (FIG. 7c).

Alternatively, a haptic portion can be in any shape or form and be constructed of any material such as silicon or rubber. It can be part of a knob, collar or ring along any portion of the handle and used to deflect, torque, move one or more portions of the distally located catheter/instrument.

Figure 12:
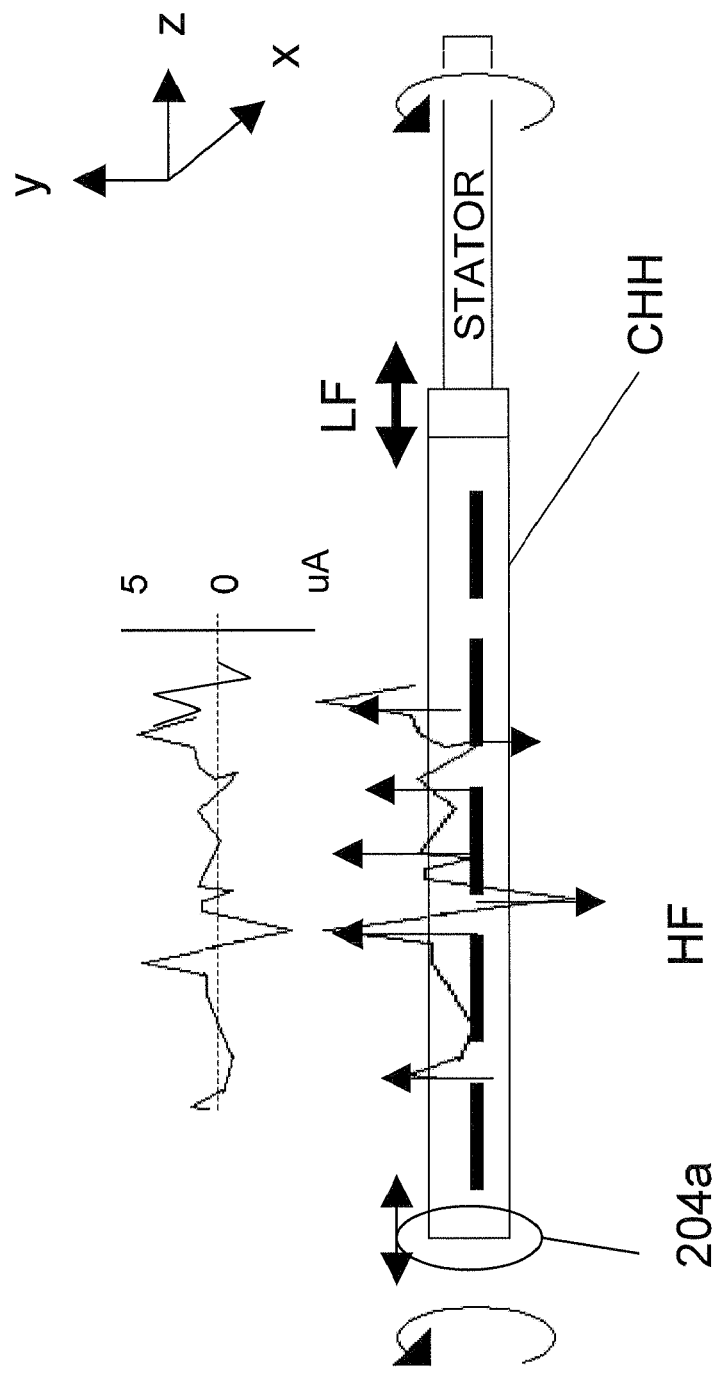
FIG. 12 one or more linear displacement motors, LF, which moves to and fro, in one degree of freedom (1-DOF) coaxial to the inserted catheter, is driven by the low frequency component of the current signal, I. One or more high frequency motors, HF, imparts high frequency information for reproduction of vibrotactile information to the HH (up and down arrows). A knob or collar mechanism at the distal CHH provides temperature or texture information and serves to deflect or maneuver one or more portions of the inserted catheter.

The fine, high frequency motion of the fibrillating left atrial appendage (LAA), illustrated in FIG. 8a, is translated into a similar quality motion in the haptic handle alerting the operator that the catheter is in a location putting the patient at risk for stroke. When a sensor is within the left atrial chamber, a vibratory sensation is appreciated once the catheter is within the LAA during atrial fibrillation. See FIG. 8b for anatomic detail obtained from a two dimensional ultrasonic transesophageal view. This will have variable amplitude, vector and frequency such as the high frequency periodic movement associated with atrial fibrillation (200-500 per minute). This movement will have an envelope with changes in level, gain, magnitude relative to atrial appendage motion and the current generated by one or more distally located sensors (LAA current in FIG. 8a). An attack and fade portion ramps from the attack level to the effect's overall magnitude over the attack time. As the catheter moves from a fibrillating appendage toward the pulmonary vein the level ramps from the effect's magnitude to a fade level over a fade time corresponding to the intra-cardiac movement imposed onto the catheter's distal portion at varying locations as a function of time. Thus, as the catheter tip moves toward a pulmonary vein (FIG. 9), the vibratory amplitude will dampen. The periodic waveform can be shaped (e.g. sinusoidal, triangular, sawtooth) relative to the changes in PzN current as a function of time (FIG. 8a). Dynamic changes in spacing and bump width simulate the texture of contacted tissues (psychophysical haptic rendering discussed below). In a preferred embodiment, the higher frequency motion is tactually simulated along the body and/or at the distal end of the CHH providing the operator with physiologic information about the contractile function of the LAA and stroke risk. This can be done with regional actuators positioned at the handle's terminal portion or in one working of the invention incorporated within a knob, collar, or rotating sphere that is also used to deflect the desired portion of the inserted catheter (e.g. during positioning for ablation) as depicted in FIG. 12.

Haptic rendering will enable the operator to tactually feel fine anatomic detail and subtle dynamic mechanical characteristics (e.g. the opening and closing of a patent foramen ovale). Dynamic changes in texture/softness and appreciation of inter-atrial blood flow; the time dependent changes in resistance, elasticity, motion and thickness of the interatrial septum during the cardiac cycle; the sensation of entering of the coronary sinus os which rotates and twists with cardiac systole, the dynamic changes in pulmonary veins and the texture of the ruggae of the LAA with and without cardiac arrhythmia are examples of dynamic cardiac mechanical properties that can be detected and analyzed for diagnostic purposes.

Texture, softness, and deformation sensors at the catheter's distal portion can acquire such data. In another embodiment, texture information is augmented by using tissue softness sensors. These sensors can implement catheter based vibration-based softness sensors or deformation-based methods. The latter technique can be best realized using CMUT technology (Leng H and Lin Y. Development of a Novel Deformation-Based tissue Softness Sensor. IEEE Sensors Journal, Volume 9, No. 5. May 2009. pp 548-554). The biomechanical characteristics of human tissue relate to underlying pathology. Non-compliant vasculature and cardiac structures are associated with various pathologic states (e.g. diastolic dysfunction and diastolic heart failure in a hypertensive patient, peripheral vascular disease). Cardiac cycle dependent changes in the Young's modulus of various tissues can be obtained along with an elastodynamic assessment of tissue properties using softness sensors and tactually appreciated in the CHH.

Figure 10:
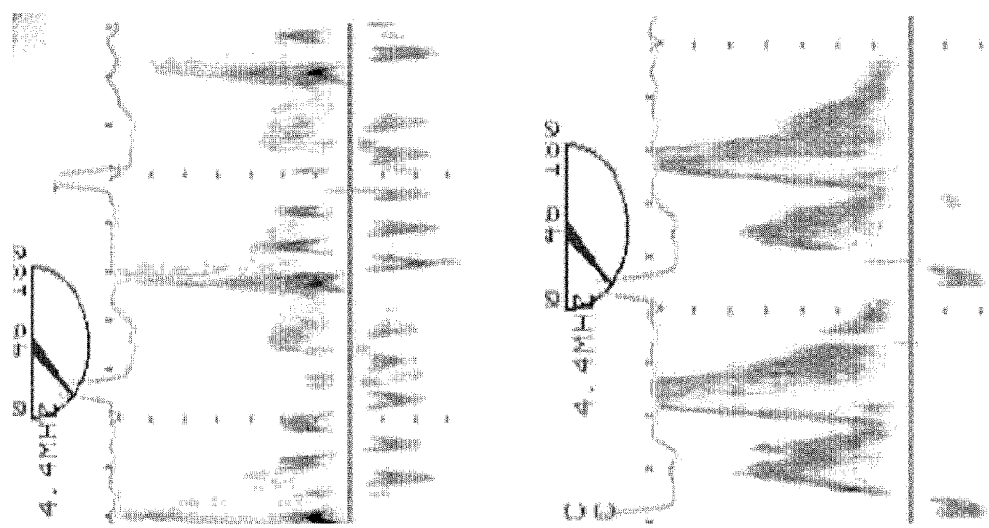
FIG. 10 once within the pulmonary vein, the fibrillatory sensation (top) will fade out and an intermittent biphasic constant motion will be appreciated secondary to pulmonary venous inflow (bottom). Haptic rendering will be very important as to maintain passivity and optimize this transition.

Tissue Doppler Imaging time graphs in FIG. 10 depict changes in the periodic waveforms as the region of interest moves from a fibrillating LAA to pulmonary vein. Once within the pulmonary vein, the fibrillatory sensation (FIG. 10 top) will change and an intermittent biphasic constant motion will be appreciated secondary to pulmonary venous inflow (bottom). Haptic rendering serves to maintain passivity and optimize the detection of this transition as is discussed below. The sampled waveforms depicted are obtained with tissue and pulse wave Doppler transesophageal recordings from sample volumes in the specified regions of interest.

Figure 11:
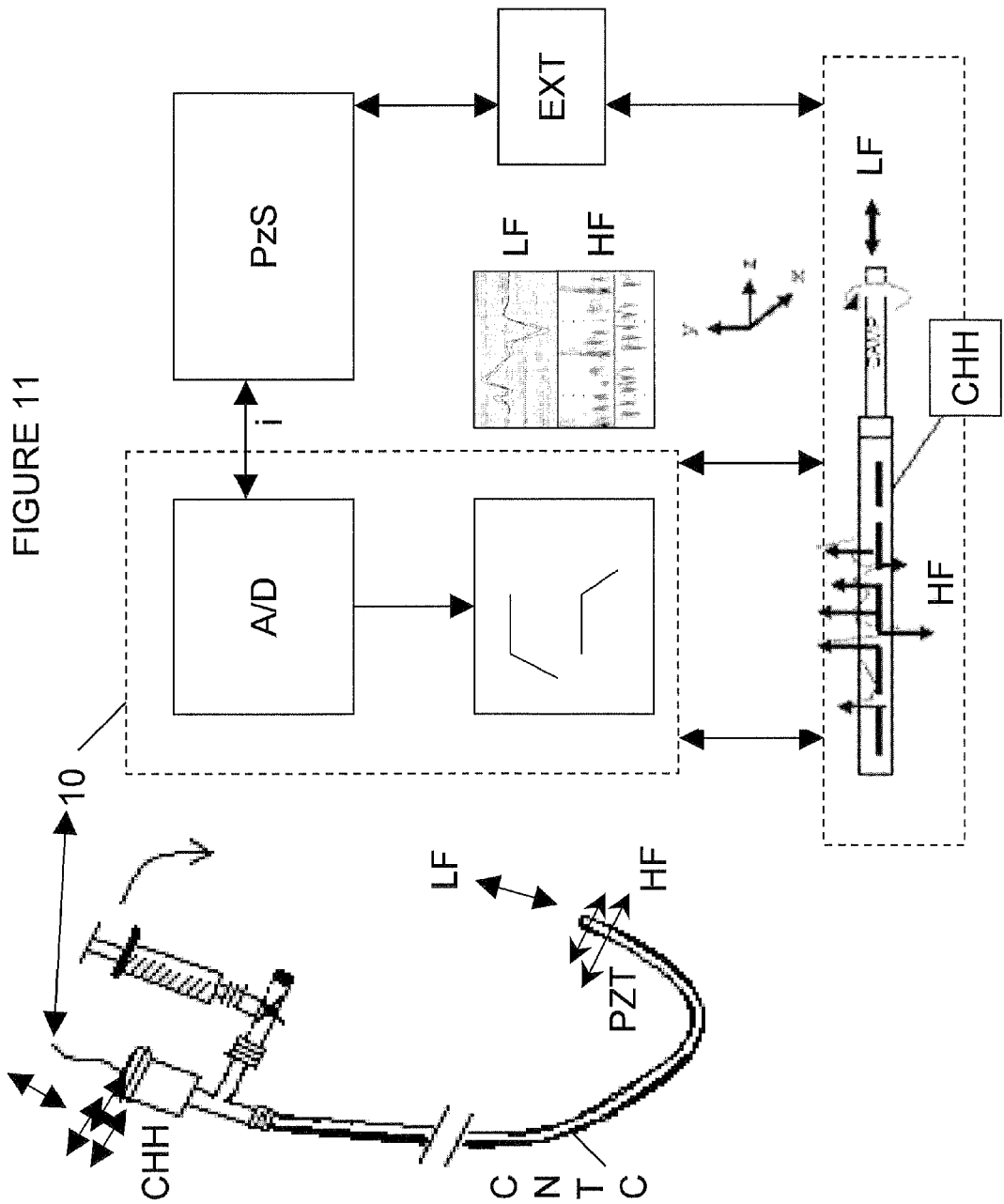
FIG. 11 is a block diagram/representation of the workings of the invention. Sensor PzS sends current signals, I, via conductor(s) (e.g. CNTC) that are A/D converted in processor 10. High/Low pass filtering separates tactile data and delivers varying frequency information to different portions of the Cardiovascular Haptic Handle, CHH. External sensing systems provide a continuous frame of reference for inserted sensor(s)/catheter and CHH in space-time. In this example, 10, is separate from the CHH reducing its bulk and the signals are transmitted via wiring, though wireless communication is within the scope and spirit of the invention.

Referring to FIG. 11, conventional conductor (e.g. used in cardiac pacing leads) or carbon nanotube conductor or hybrid CNTC is connected to the continuous film of soft PZT (PzS in figure) and directs the current signal to an amplifier or preferably processor/controller, 10. When processing/haptic rendering occurs A/D conversion of the signal is required. An example of a soft PZT is PIC 153, a modified lead zirconate—lead titanate piezoelectric ceramics material with extremely high permittivity and coupling factors, a high charge constant, and a Curie temperature of around 185.degree. C. This material is suitable for hydrophones, transducers in medical diagnostics and PZT translators. Soft PZT of the type needed (e.g. PIC 153) is manufactured by companies such as Physik Instrumente, Auburn, Mass. Other sensor designs and materials can be used and in no way is the scope and spirit of the invention limited to a specific sensor type.

High, low and band pass filtering occur and specific components within the CHH tactually simulate the motion of the tissue in contact with the catheter's distally located sensors (or EXT). One or more microfabricated linear and/or rotary displacement motor(s) or similar actuators are contained within the CHH. An example of such a motor is the M-674-K High Precision Z Actuator for Bio-Automation manufactured by Physik Instrumente, Auburn, Mass. Alternate constructs for linear and rotary motors may be used as well. The motors have large torque or force to weight ratio, high holding torque or force, high positioning resolution, short response time, low input voltage, operation independent of the magnetic environment, and compact and gearless design. Bouchiloux et al describe the design of rotary and linear ultrasonic motors with free stators that are suitable for aerospace and robotic applications which can be implemented as well (International Center for Actuators and Transducers, Penn.State Univ.).

A simplified CHH accommodates one or more (preferably microfabricated) tactile feedback motor(s) comprised of a 1-DOF, linear displacement low frequency, LF, motor and one or more higher frequency motors, HF, with shaft and weights mounted as components within the catheter handle for tactually providing vibration/displacement information to the operator's hand (e.g. as illustrated in FIGS. 11 and 12). By way of example, (FIG. 11) one or more linear displacement motors or other types of actuators, LF, which move to and fro, coaxial to the inserted catheter, driven by the low frequency component of the current signal, I. One or more high frequency motors, HF, imparts high frequency information for reproduction of vibrotactile information to the HH (up and down arrows). A tunable band pass filter (e.g. within processor 10) directs signals between 0.33 Hz and 3 Hz to LF and signals between 3 Hz and 10 Hz to the HF. LF is designed to reproduce the normal motion of contracting myocardium during phases of the cardiac cycle. HF reproduces pathologic high frequency motion that occurs during arrhythmias (e.g. atrial fibrillation).

In more complex embodiments of the invention, simultaneous appreciation of multiple physiologic properties (e.g. multiple frequency information) may occur. For example, the system can relay variable vector, cardiac cycle dependent longitudinal, radial or torsional displacement information. In one application, the operator will have an appreciation of the resistive force upon an excimer laser or alternate extraction system during extraction procedures. Sensors at the distal portion of a permanently implanted lead being extracted from an atrial chamber will be subject to vibrations from atrial arrhythmia and backward coaxial tension as a result the lead being pulled from the intracardiac tissue. If the sensor is proximate to myocardium, systolic and diastolic contractile properties will be appreciated and force feedback will ensure that the operator applies the appropriate amount of pressure at critical time frames. Fourier transform analysis of acquired signals can be implemented in processor 10 which delivers specific signals characteristic of specific anatomic regions to different actuators within the CHH. These data can be saved and used for data storage (EMR) and for educational purposes.

In a simplified multidimensional mode, amplifiers receive signals from one or more sensors and amplify and provide the signals (5 in FIG. 1) to the HH actuators. For example, one of the three sets of PzN (e.g. FIGS. 4a and 4c: electron micrograph image of helical carbon nanotube constructs, ZnOxide radial nanowire nanogenerators) is oriented along the longitudinal axis of the lead or catheter (z axis) and two other sets are oriented orthogonal (x, y axes) as illustrated in FIG. 4b by the dotted arrows. Alternate types of sensors such as triaxial fiberoptic force sensors found in catheters manufactured by Enclosense SA of Geneva, Switzerland, can be used to acquire data and input to processor 10 and in no way are the inputs limited to piezoelectric technologies. More than one sensor type can be implemented and indeed, various sensors may be used that are specific to the nature of the motion data being acquired (e.g. related to bandwidth). In this example, the degree of displacement and frequency of displacement of PzN is proportionate to the action provided by the three motors within the catheter handle. Motion is multidimensional, rotational and to and fro (coaxial). The motion (up and down arrows, y axis) is appreciated along the full length of the handle and is proportionate to the sensor's current amplitude. The gain of the handle's motion is adjustable in all dimensions (as is the force feedback) but always proportionate to catheter displacement/motion at its distal sensor. For optimal reproduction of tissue mechanics, omni-directional vibration/displacement and torque of the catheter tip detected by one or more catheter based PzNs (or other sensors) is transmitted to the handle of the catheter which can be used for positioning and manipulating the inserted catheter (virtual catheter design).

In one mode, the haptic display is a simplified version of an ordinary handle as known by those experienced in the art which incorporates tactile feedback mechanisms. By way of example, a collar, or trigger mechanism (204a in FIG. 12) at the end of the catheter that is conventionally used to torque/manipulate the angle of the inserted catheter/instrument is constructed to reproduce cardiac tissue motion. This motion can be a simulation of the high and/or low frequency component of tissue motion. Alternatively, the collar/trigger mechanism can reproduce the low frequency motion and the handle body simulates the high frequency motion. The collar/trigger mechanism can be employed to provide texture and temperature information and finely detailed temporal information (e.g. vibratory motion), as well as, a simulation of motion of the catheter's joints (e.g. torque, pitch, yaw) during deflection of the handle's collar(s) as this is the portion of the CHH that is in contact with the operator's fingertips.

Sensor Orientation/Frame of Reference

Navigational systems (e.g. EnSite NavX, and MNS, Niobe, Stereotaxis, St. Louis, Mo.) or satellite systems (e.g. GPS) for performing ablation as known by those experienced in the art wirelessly detect sensor orientation (e.g. via magnetic, electromagnetic field, resistive/impedance data) relative to the position of the distal portion of the catheter and essentially maintain a proper frame of reference in real-time. Thus, intrinsic and extrinsic systems (EXT) function in a supportive fashion. This data is input to processor 10 (along with information regarding the CHH's position in space-time) as to maintain an accurate representation of sensor locations and CHH position in three dimensions, thereby replicating the same in the CHH in real time (double arrows in FIG. 11). Navigational systems can be implemented along with a plurality of alternate technologies to locate catheter and the CHH position and facilitate real time appreciation of catheter motion with the CHH. This is communicated to the operator along with a three dimensional real-time representation of intracardiac anatomy. In a preferred embodiment, multiple sensor sites (nodes A, B, C, D) are tracked using EXT. This can be done, by way of example, using an externally applied electrical field and measurements of impedance changes at each node in real time or alternate methodology. Each node is composed of multiple sensors that reference real time position relative to EXT and relative to other nodes along the inserted catheter. Thus, three dimensional localization occurs at multiple points along the inserted instrument and the system then provides the operator with determinations of motion and forces (e.g. pitch, yaw, torque) along nodal locations. These data are input to the processor, 10, and serve to generate tactual representation of catheter and contacted tissue motion to the HH (e.g. virtual catheter). Deployment of multiple nodes in a contiguous fashion will facilitate simulation of full length catheter motion (distal end) in a hand held virtual catheter with similar physical characteristics (proximal end) as illustrated in FIG. 7a. The operator holds a simulated version of the catheter's distal end that looks and feels the same as the inserted distal end (e.g. same elasticity/bendable joints) and while he or she manipulates the distal portion the proximal portion moves and deflects in a likewise fashion with the same force vector and magnitude along multiple joints or nodes The motion and forces imparted to both ends is the same ("virtual" coupling) and bi-directional communication of the catheter's and CHH's three dimensional position provides continuous feedback for position frame of reference (FIG. 11—double arrows and see below). CHH localization can be done with positioning systems including but not limited to satellite type GPS, thermal, electromagnetic, haptic glove, electromagnetic, resistive fields. Thus the cardiac tissue causes the handle to move torque/bend/vibrate etc. and the operator feels this in the CHH while the operators actions similarly affect the distal end effectively bridging the gap caused by attenuation of intervening soft tissues, catheter flexion/dampening and gross operator movement.

In one mode of the invention, intrinsic sensors are not needed for data collection and tactile simulation is provided solely by data collected by extrinsic means (non-invasive modalities). This is depicted in FIG. 1 as input, EXT. The extrinsic methods for collecting motion data include but are not limited to magnetic, resistive, thermal, electromagnetic/ optical or impedance based navigational systems, ultrasonic/ radiographic imaging. Real-time localization data output from three dimensional navigational systems imaging technology (e.g. intracardiac ultrasound), or alternate positioning systems (e.g. magnetic, electromagnetic, optical, impedance-based, or alternate global positioning system techniques) is input, IN, to the controller, 10, and used to drive the HH. Neural networks can be used to "teach" and translate analogous data sets between intrinsically and extrinsically acquired data as to facilitate the understanding of novel tactile metrics and for optimization of system function as described herein and in the author's co-pending patent applications (Ser. No. 11/334,935).

Cardiovascular Haptic Handle—Basic System Design

Figure 17:
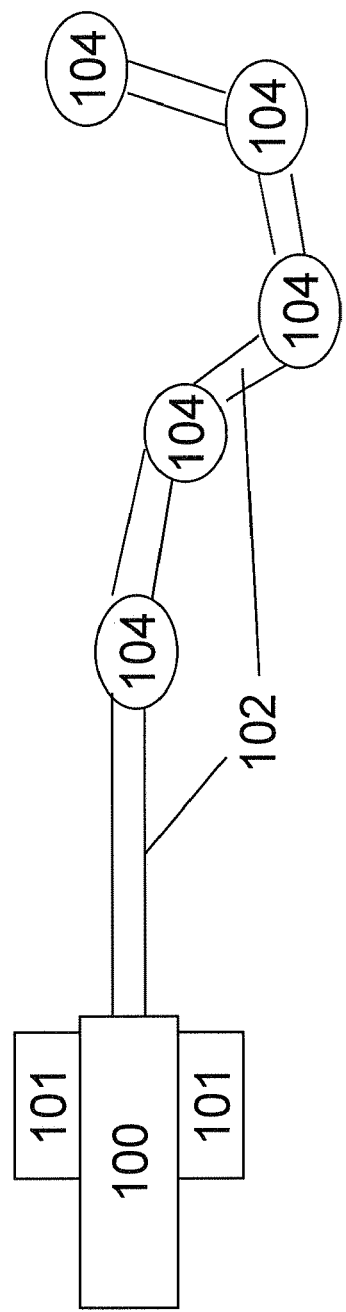
FIG. 17 shows a somewhat simplified view of a haptic handle system constructed in accordance with this invention.
Figure 18:
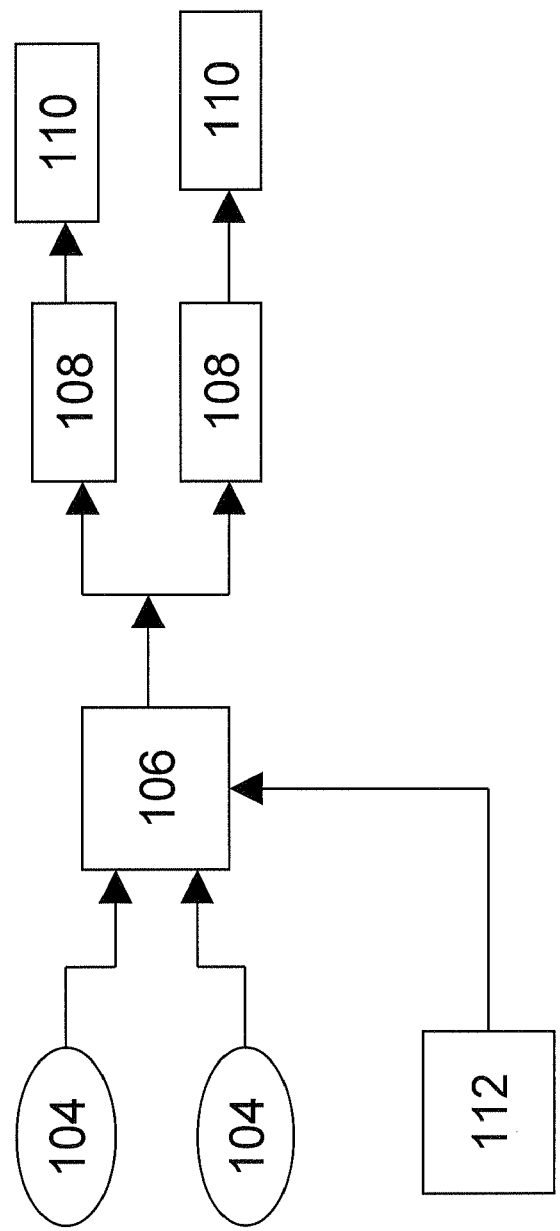
FIG. 18 shows a block diagram for the system of FIG. 17.

Briefly, as shown in FIGS. 17 and 18, in one embodiment, a haptic catheter system constructed in accordance with this invention includes a handle 100 with an elongated element 102 sized and constructed so that it can be inserted into the body of a patient to sense and probe a particular tissue or organ. Sensors 104 are disposed either at the tip of the element 102 or at the tip and along its length as shown. Sensors 104 can be internal electrodes that are used in conjunction with surface electrodes placed on the patient's body along three orthogonal axes for emission of a low current, high frequency electrical field used to determine electrical potential/field strength for electroanatomic mapping as known by those skilled in the art (e.g. EnSite NavX; St. Jude Medical, Inc., Minneapolis, Minn.). The haptic handle 100 is provided with a plurality of mechanical controls 101 that are manipulated in a conventional manner by an operator as the element 102 is inserted into the body to cause it or its tip and/or alternate portions to move, rotate, etc in conjunction with the sensed cardiac tissue motion. In one embodiment, sensors 104 are at least in part located at movable pivot points or joints along element 102, move in unison with comparable joints in 100 and determine forces and motion characteristics of element 102 and of tissues in contact at sensor sites, 104 as described in more detail below.

As shown in FIG. 18, signals from the sensors 104 are provided to a digital signal processor (DSP) 106 either through wires imbedded in the element 102 or wirelessly, in which case, some preliminary signal processing and encoding is performed within element 102 and/or the sensor 104. The DSP 106 can be incorporated into the haptic handle, 100, or can be remote to reduce the bulk and size of the haptic handle, 100.

The DSP 106 analyzes these signals and sends control signals to actuators 108. These actuators then activate one or more tactile elements 110 to provide live, real time tactile sensations to the operator representative of cardiac motion characteristics. The actuators 108 are preferably incorporated into the body of haptic handle 100. If necessary, the haptic handle 100 is made large enough so that it can be held with two hands, with each of the hands contacting some of the tactile elements 110 whereby one hand can get tactile sensations (e.g. cardiac twist) corresponding to the signals from one set of sensors and the other hand can get tactile sensations from the rest of the sensors.

In one embodiment of the invention, one or more external locator systems 112 are used to locate the catheter and its distal end within the body in real time. The information from these system is used alone or combined with information from the sensors 104 to generate the control signals for the actuators, 108 and in one preferred embodiment, provide a three dimensional frame of reference such that the hand held handle 100 is positioned appropriately in space-time during the cardiac cycle (as described below).

Figure 19:
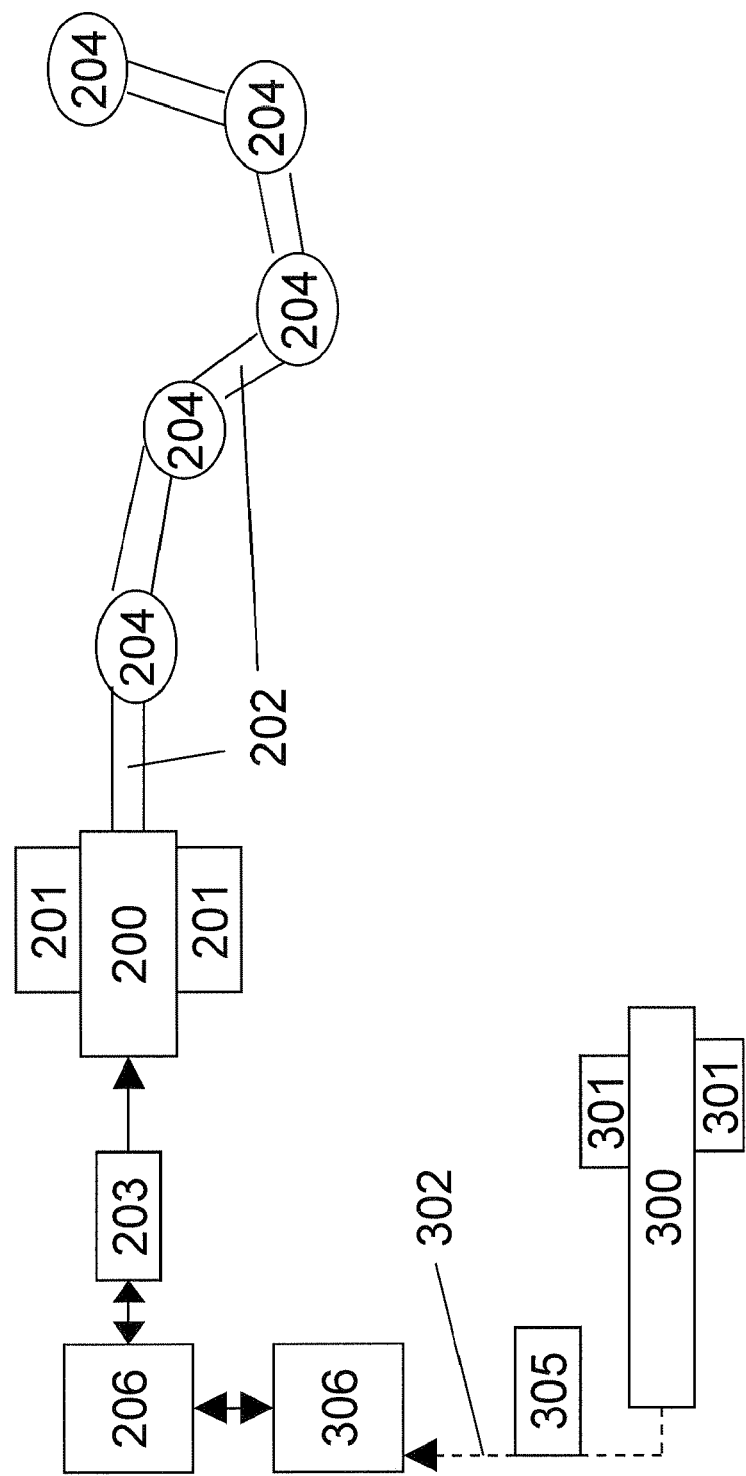
FIG. 19 shows an alternate embodiment in which a local catheter and handle and sensors are monitored, and optionally, operated by an operator at a remote location using a simulated haptic catheter.

FIG. 19 shows another embodiment of the invention. In this embodiment, there are two separate groups of components provided, one group being disposed locally and the second group being disposed remotely. The local group includes a catheter with a handle 200, mechanical controls 201, with manipulating actuators 203 and an elongated element 202 with sensors 204. The information from the sensors 204 are fed to a local processor 206.

The remote components include a remote processor 306, and a remote haptic handle 300. Within the haptic handle 300, tactile elements are provided which are actuated by actuators (not shown). In one embodiment, the processor 206 either transmits the sensor signals to the remote processor, 306, which then processes these signals and generates control signals for the actuators in the haptic handle, 300 and mechanical controls 301. Alternatively or additionally, the sensor signals are processed by the local processor 206 and used to generate control signals which are then transmitted to the remote processor and used to control the actuators. In either case, external navigational systems may also be used as in the previous embodiments, however they are omitted here for the sake of clarity.

In another embodiment of the invention, depicted in FIG. 19, the haptic handle 300 is associated with either a remote, wireless connected system (302) or a detachable elongated element 302 which is a physical simulation of the element 202. Additional catheter actuators 305 are provided that are also controlled by commands from processor 306 (and/or 206) and in response to these commands, the actuators 306 cause the elongated member 302 to take on the shape and/or move exactly in the same manner as the element 202. Therefore an operator can look at and feel the member 302 and get a visual and/or tactile indication of what is happening at and with element 202.

Figure 20:
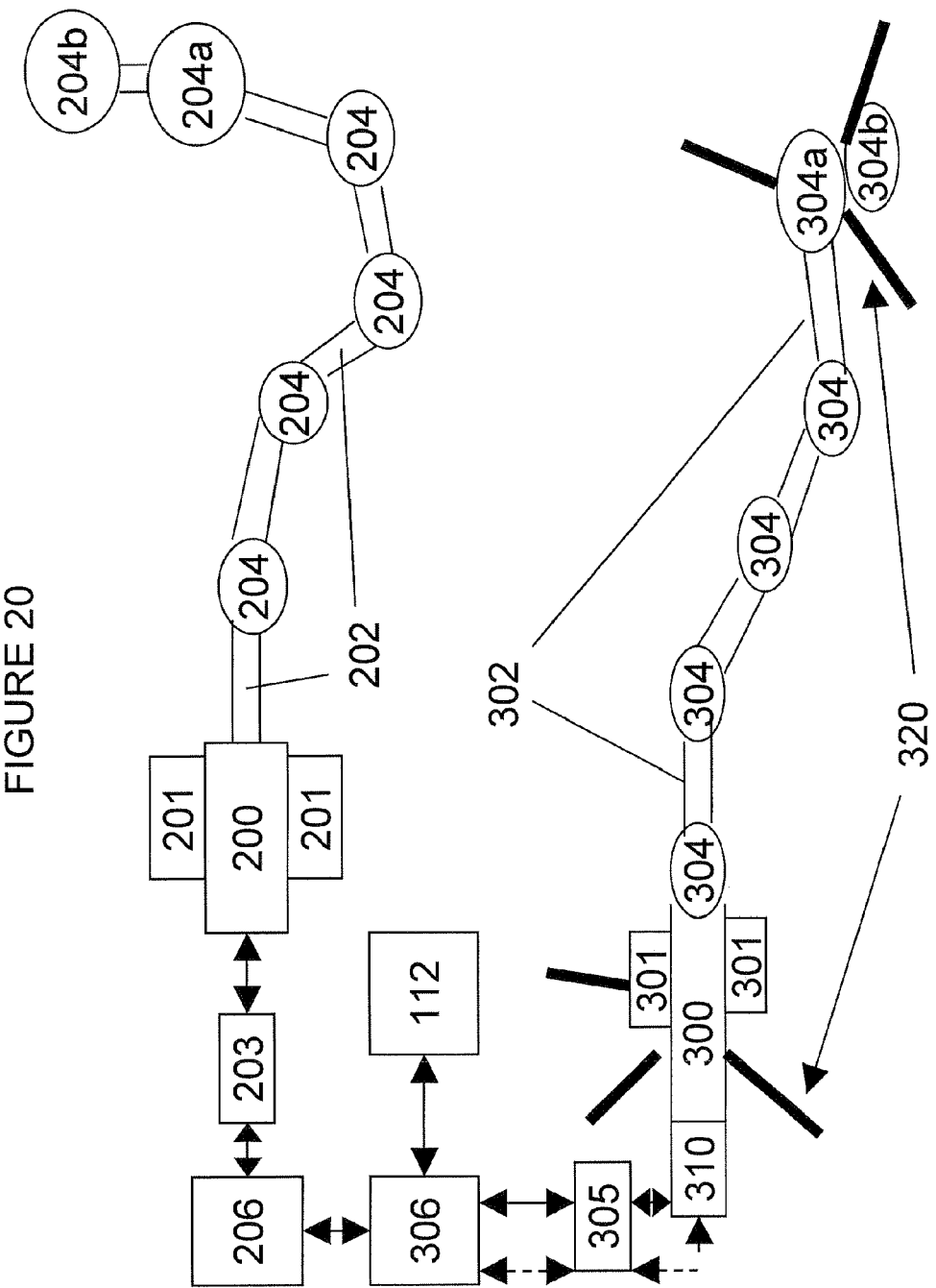
FIG. 20 shows an alternate embodiment descriptive of a virtual catheter.

In yet another embodiment of the invention, depicted in FIG. 20, the haptic handle 300 is also provided with manipulating controls 301 similar to the controls 101 in FIG. 17. The operation of these manipulating controls is sensed within the handle 300 and movable joints 304 and corresponding control signals are transmitted to the processor 306 which then transmits them to the processor 206. The processor 206 sends corresponding commands to another set of actuators 203 which are coupled to mechanical controls 201 on the handle 200. In this manner, an operator or operators can manipulate the controls 301 and 304 locally and/or at a remote location and the actions are transmitted through processors 306, 206 and actuators 203 to controls 201 thereby allowing the operator to manipulate and operate the catheter element 202 locally and remotely. As illustrated, sensors can be located at one or more pivot points or joints, 204 and 304, in the catheter, 202, and virtual catheter, 302, respectively. Thus, the dynamic action of the surrounding tissues and vasculature on 202 during the cardiac cycle, and of operator's actions on 302 are reciprocal and sensed forces and motion at 204 and 304 are coupled. Sensor 204a and temperature texture knob, collar, ring or sphere and the like controller/actuator 304a are distally located on catheter 202 and handle 302, respectively and provide highly detailed sensed information at the operator's fingertips including but not limited to texture, softness, high frequency low amplitude vibration and control of the catheter's most distal aspect. Delivery of therapies occurs at 204b (e.g. radiofrequency ablation) is controlled with actuator 304b or alternate controller and is protected from sensor 204a by an insulating mechanism and adequate distance. Communication between sensors, actuators and controllers is bidirectional. Data acquired can be stored in processing centers 400 and 1000 (FIG. 1) for electronic medical record keeping, academic pursuits and teaching purposes.

In one embodiment, three mechanical controls/lever arms, 320 (bars FIG. 19), are positioned orthogonally or roughly orthogonally to one another about the terminal portions of the otherwise free-floating, hand held haptic catheter, 302 and position 302 with the proper frame of reference relative to the three dimensional spatial orientation of inserted catheter 202. Position information is compared in real time with internal sensors 204 and the handle's position sensors present in joints with mechanical controls at 304 along with external locator system(s), 112 and send signals to mechanical controls/lever arms 320 and within 304 as to correctly orient 302 in space time using mechanical controls/lever arms 320. The system thereby accounts for patient position, bodily motion and even geomagnetic forces in real time.

In all the systems described above, the sensors are used to determine in vivo dynamic characteristics of a specific tissue or a specific moving organ. Dynamic characteristics include various parameters related to motion of an immediate portion of the tissue or motion of the catheter with respect to its surroundings, such as displacement, velocity, acceleration, oscillation amplitude, frequency, phase, etc. and the effect of an inserted instrument on such motion.

Haptic Rendering

The limits due to sensor performance characteristics have historically exceeded the limits due to computation. The improved performance characteristics of current sensor technologies will enable haptic synthesis to take full advantage of the currently available and emerging computational techniques for haptic synthesis for the manufacturing of a fully transparent tactile force feedback system. For more sophisticated versions of the invention, complex haptic rendering techniques are implemented within processor, 10. The haptic interface is designed to function over a wide range of dynamic impedances. The dynamic range of impedances that can be rendered by the haptic system while maintaining passivity should be large (i.e. high Z width) as to optimize the virtual experience (see below). Impedance in this context is defined as a dynamic relationship between velocity and force (Otaduy M A. Haptic Rendering; Foundations, Algorithms and Applications. A. K. Peters Ltd. 2008). Passivity design is necessary in order to combine a continuous-time mechanical system with a discrete time controller. This can be best understood in its application to passive rendering of a one degree of freedom haptic interface such as a virtual deformable wall subject to perforation (e.g. interatrial septum, atrial or ventricular free wall, vasculature obstruction) as described below. Physical and electrical means for optimizing Z width (e.g. damping mechanisms) are applied as needed to optimize functionality of the controller. Additionally, psychophysical techniques can act to alter the user's perception of the impedance range of the haptic control system including methods of rate hardness and event-based rendering as described in the references provided and in more detail below.

The haptic control system is a sampled-data system subject to error when used to monitor and simulate a dynamic process (e.g. cardiac systole). The effects of sampling can cause the system to lose passivity even with optimal sensor and actuator design (Colgate E, Schenkel G G. Passivity of a Class of Sampled Data Systems: Application to Haptic Interfaces. Journal of Robotic Systems 14:1 (1997) 37-47). Examples of how to maintain passivity in a sampled-data system (e.g. discrete-time control model) can be found and best understood by considering an analytical passivity criterion for a one degree of freedom haptic interface (e.g. catheter motion opposed to a virtual deformable wall). The discrete-time controller model includes a unilateral constraint operator and is inclusive of A/D and D/A conversion in the feedback loop. The unilateral constraint is a simple form of contact and collision between two objects. It serves well for understanding how the needed virtual environment applies directly to the needed haptic interface for performing cardiac procedures (e.g. ablation of arrhythmia and catheter manipulation). More complex models can be designed (e.g. Abbot J J, Okamura A M. Effects of Position Quantization and Sampling Rate on Virtual Wall Passivity", IEEE Transactions on Robotics 21:5 (2005), 952-964) and applied to develop the haptic systems described herein and are also discussed below (e.g. intravascular navigation).

In this invention, we will refer to a virtual deformable wall as meaning one or more cardiac or vascular structures. By way of example, the virtual wall model will fit anatomic structures such as the interatrial and interventricular septum, myocardial tissue at various intracardiac and extracardiac locations, the ventricular free wall. These are not static structures and are constantly moving during normal and pathologic conditions. In one model, the system's ability to simulate the dynamic intracardiac environment is in part based on derivation and implementation of the appropriate translation function (developed by the inventor and described in the parent and co-pending patent applications) from analogous data collected with alternate means (e.g. electromagnetic three-dimensional catheter navigational systems) and/or from other data acquired in situ or ex vivo in the laboratory. Correlations drawn by comparing analogous data acquired from intrinsic and extrinsic systems enable neural networks to be applied for this purpose and serve to calibrate the sampled data to some standard or referenced metric. Through these techniques we will better understand the physiologic relevance of data collected with varying haptic interfaces in different populations of patients.

Haptic Rendering

Haptic Interface

Figure 13:
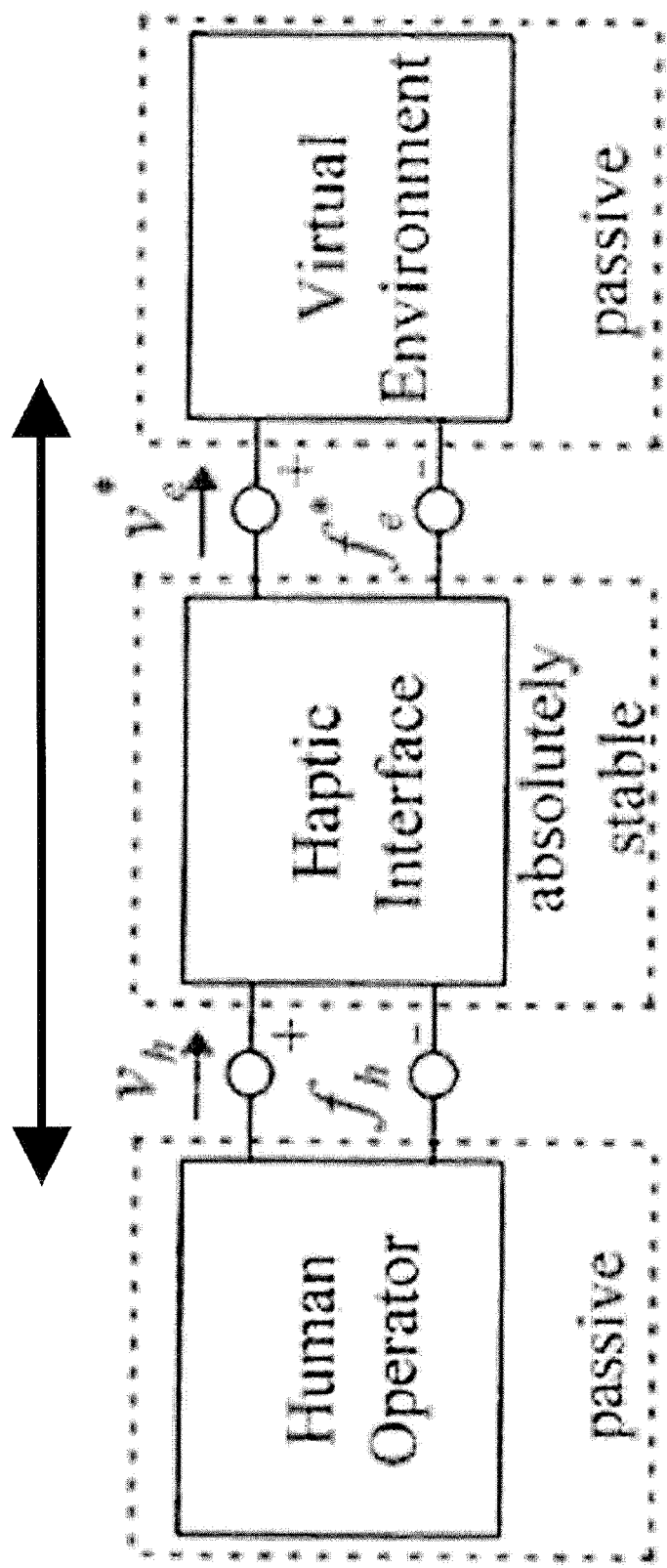
FIG. 13 the network model of haptic simulation.
Figure 14:
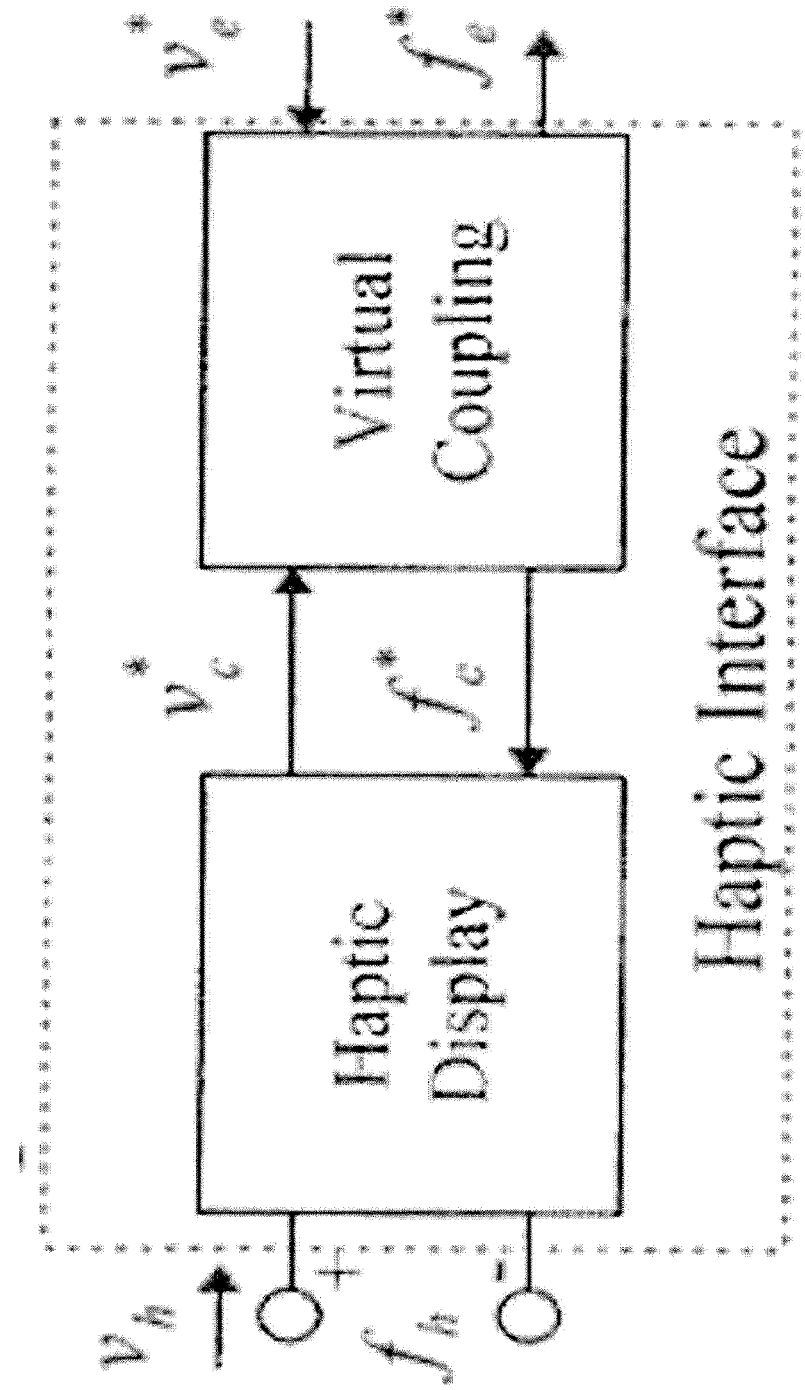
FIG. 14 the haptic interface
Figure 15:
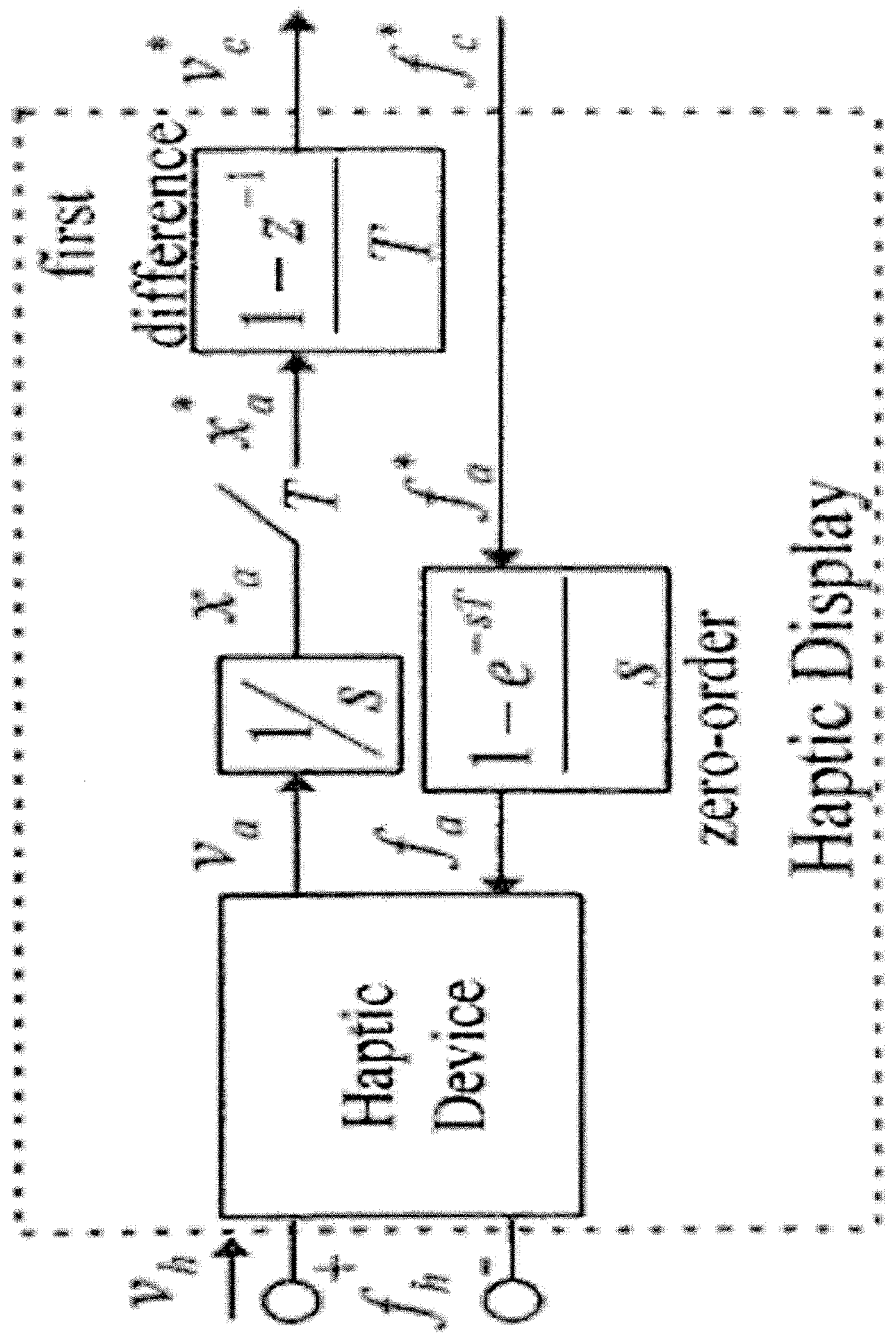
FIG. 15 zero order haptic display

The type of haptic display used will depend in part on the type of sensor used for data acquisition. This is illustrated in FIG. 13, the network model of haptic simulation. The haptic interface is between the human operator/haptic handle and in situ cardiac tissue rather than a virtual environment which is what is conventionally understood in the field of haptics). In this invention, coupling is not virtual as the human heart and vasculature follow the laws of physics and are passive systems. This renders the total system to be completely transparent. Processing and haptic rendering techniques used to optimize the operator's tactual experience renders the system virtual. The extent that the system is virtual (degree of virtual coupling) is dependant upon the type of sensor(s) used, frequency of sampling, and amount of signal post-processing that occurs. The fundamental difference between the workings of this invention and conventional haptic interfaces is that this technology The haptic interface (FIG. 13) can be part of an impedance or admittance display depending on whether or not the system measures motion and displays force or measures force and displays motion. Admittance haptic devices simulate mechanical admittance by reading force and sending position information. Impedance haptic devices simulate mechanical impedance as they read position and send force data. The latter is suitable for extrinsic sensors such as three dimensional navigational systems and the former for intrinsic sensors including but not limited force sensor technology. The workings of the invention are such that either or both admittance and impedance displays can be used as the haptic interface (FIGS. 14 and 15). The optimal construct will provide for a nearly passive system that has near absolute stability (as both the operator and sampled environment are passive). That is, the virtual environment is a physical construct (i.e. haptic handle) rather than a computer model as known in the gaming industry. Once haptic rendering is used in the processing of acquired data, the environment becomes virtual as the interface between the sensor and display uses digitized information and data is sampled with discrete variables and is, as such, not truly passive.

In the most simplified embodiment of the invention (hybrid high/low frequency haptic handle), a truly passive system is present when there is pure amplification of acquired sensor data (e.g. PzS current signals) and delivery of current directly to motors housed within the haptic handle without processing or ND conversion. For the more complex haptic handles (virtual coupling), system transparency becomes more costly.

Haptic Rendering

Destabilizing Effects of Sampling

Sampling prevents detection of the exact time when the haptic display contacts a dynamic tissue surface. Sensor quantitization causes a loss of information due to sensing only discrete changes in the value of the acquired signal while sampling introduces uncertainty with respect to event timing between sampling intervals. The latter is not dependent on sampling frequency while the former is. Position sensing resolution has the effect of quantizing penetration distance into the tissue surface. In one embodiment, the system purely relies on pure analog data (or during specific time frames) and thus is passive and transparent. Thus, minimal processing will improve coupling as both cardiac tissue motion characteristics and human control of the catheter are passive, bound by laws of physics. A simplified approach will reduce the full effect that may be realized with sophisticated haptic rendering (e.g. texture appreciation) and virtual simulations but should eliminate system instability.

Quantization limits the performance through velocity estimation as well. Rapidly varying velocities lead to instability. Low pass filtering the resulting velocity signal smooths out the acquired data. Filtering, however, leads to system instability secondary to increased time delay and phase distortion. Butterworth filters, which compute a velocity based on a weighted sum of raw velocity signals and past filtered velocity estimations, can be used to improve system stability. Heavy filtering comes at the cost of reducing the systems ability to detect and display transient responses. In one mode of the invention, filtering intensity and characteristics can vary according to anatomic location. Location can be inferred by assessment of other data acquired intrinsically or determined using extrinsic systems such as navigational technologies. Other filtering techniques are within the scope and spirit of the invention and may be applied to prevent errors in velocity signals (e.g. first—order adaptive window length) as described in Janabi-Sharifi F, Hayward V, Chen C J. Discrete-Time Adaptive Windowing for Velocity Estimation. IEEE Transactions on Control Systems Technology 8:6 (2000), 1003-1009.

Destabilizing errors lead to an active rather than a passive system. Virtual coupling will help improve the accuracy of the haptic display. Virtual coupling links the haptic display and virtual environment and consists of a virtual spring and virtual damper in mechanical parallel. This enables a lack of passivity in the virtual environment while maintaining overall system passivity. Thus, virtual coupling renders the virtual environment to be discrete-time passive. In the workings of this invention, one or more methods of virtual coupling are used to ensure optimal passivity and to extend the passivity limit of perceived tissue stiffness (virtual stiffness) during the cardiac cycle. The virtual stiffness limit is also affected by friction and quantization interval. These introduce what is termed energy leaks into the system. A variety of techniques may be used to limit energy leaks and provide the operator with the perception of a good feeling virtual environment. Psychophysical methods and passivity controllers/operators are examples of methods to improve the haptic display.

Haptic Rendering

Psychophysical Methods—Detection of a Boundary

Figure 16:
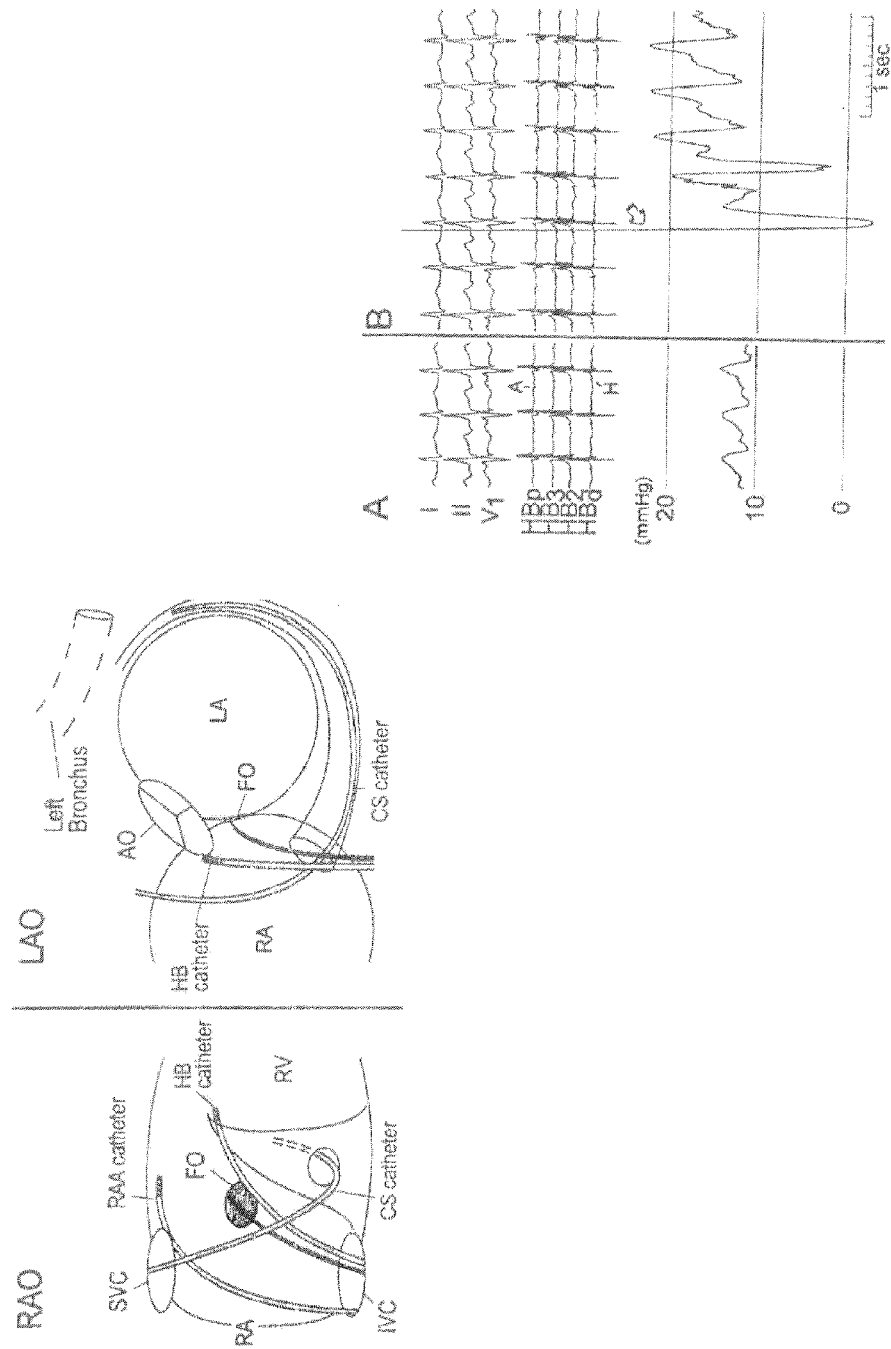
FIG. 16 top left is an anatomic rendition of how a catheter or needle traverses the interatrial septum in a left anterior oblique (LAO) view. The bottom demonstrates pressure recordings during this manipulation and the effect of catheter fling.

A rendering method for delivering a "braking pulse" upon contact with a boundary (e.g. interatrial septum) can be applied so that the force of the braking pulse occurs in one or more sampling period(s) (Salcudean S E, and Vlaar T D. On the Emulation of Stiff Walls and Static Friction with a Magneticaly Lievtated Input-Output Device. Transactions of the ASME: Journal of Dynamics, Measurement and Control 119:1 (1997), 127-132.97). High level damping occurs when crossing the wall boundary (e.g. interatrial septum) but is not sustained. A spring-damper virtual wall with virtual stiffness and damping can be applied and function to simulate perceived wall stiffness and thickness which varies during cardiac systole (e.g. increased myocardial thickness and stiffness at end-systole). Thus, by way of example, the operator can appreciate the sensation of the catheter tip fling (FIG. 16 bottom) as the catheter course across the interatrial septum (FIG. 16 top) while maintaining an awareness of being opposed to and then penetrating the interatrial septum (thickness, stiffness), crossing the septum (spring) and finally being within the left atrial cavity (enclosure) despite cardiac cycle dependent changes in tissue properties. Gathering sensor data from multiple transeptal punctures (intrinsically acquired) simultaneously with extrinsic methods (radiographic, ultrasonic, electromagnetic navigational systems) will optimize system design by fine-tuning the amount of (mechanical and/ or electronic) damping required and determining the force/ duration of the braking pulse during catheter manipulation across moving septal walls. Elimination of extraneous forces on an inserted catheter/instrument is accomplished with multiple sensors enabling system processing to subtract motion data from unwanted regions and extract the relevant tactual data.

Other methods for improving perception of contact and penetration are within the scope and spirit of the invention. Reproduction of the high frequency vibration of catheter fling when crossing cardiac/vascular tissue can be achieved by gathering multiple data sets from repeated laboratory experiments while the operator can appreciate the sensation of contacting and penetrating cardiac tissue without attenuation in the laboratory (i.e. with no intervening tissues between catheter handle and distal sensors) while data is acquired as to tune the parameter of the vibration signatures (Okamura A M et al. Reality Based Models for Vibration Feedback in Virtual Environments. ASME/IEEE Transactions on Mechatronics. 6:3 2001 245-252.). Alternatively or additionally, this comparison can be made by simultaneous data analysis of intrinsically and extrinsically acquired data. Thus, methods for accurately modeling reality-based vibration feedback can be facilitated using experimentally acquired data (Kuchenbecker K J. Characterizing and Controlling the High Frequency Dynamics of Haptic Devices. PhD Thesis Stanford University Department of Mechanical Engineering. 2006).

Haptic Rendering

Passivity Controller/Observer

Passivity controllers are another means of improving the functionality of a sampled-data haptic system. Passivity controllers increase the nominal impedance of the haptic display by counteracting energy leaks. Passivity observers and controllers stabilize haptic interaction with a virtual environment. (Hannaford B et al. 3—Stable Control of Haptics. In touch in Virtual Environments: Proceedings USC Workshop on Haptic Interfaces, edited by Margret McLaughlin. Upper Saddle River, N.J.: Prentice Hall, 2001). Passivity observers, PO, analyze system behavior and track the energy flow between elements to estimate errors introduced into the sampled-data systems while passivity controllers, PC, act to dissipate excess energy by adjusting the impedance between elements in the system (e.g. injecting additional damping to dissipate energy). This improves upon virtual coupling. Virtual coupling constantly moderates the feel of the virtual environment whereas PO/PC only do this if an energy correction is needed. The expected non-linearity of the morphologic and physiologic features of the created intracardiac virtual environment (Intracardiac Tactile Exploration System described in the authors co-pending patent application) makes exact calculation of energy flow into the virtual environment difficult. Thus, general and specific passivity observers serve as an energy model used as an energy tracking reference. The characteristics of these energy models vary according to the structural and frequency dependent features of the contacted tissue. Data acquired from multiple tissue samples in vivo using extrinsic techniques (e.g. ultrasonic, radiographic, optical, electromagnetic) are compared to analogous data acquired with the haptic system's sensors (e.g. intrinsic piezoelectric nanosensors). These data are used to compose such energy models. Thus, the translation function derived by the correlative methods outlined in the author's co-pending patent applications can be effectively implemented for this purpose. This will be especially important for recreating frequency specific information related to active and passive motion/deformation of real-time intracardiac structures (e.g. interatrial septum, left atrial appendage).

Figure 9:
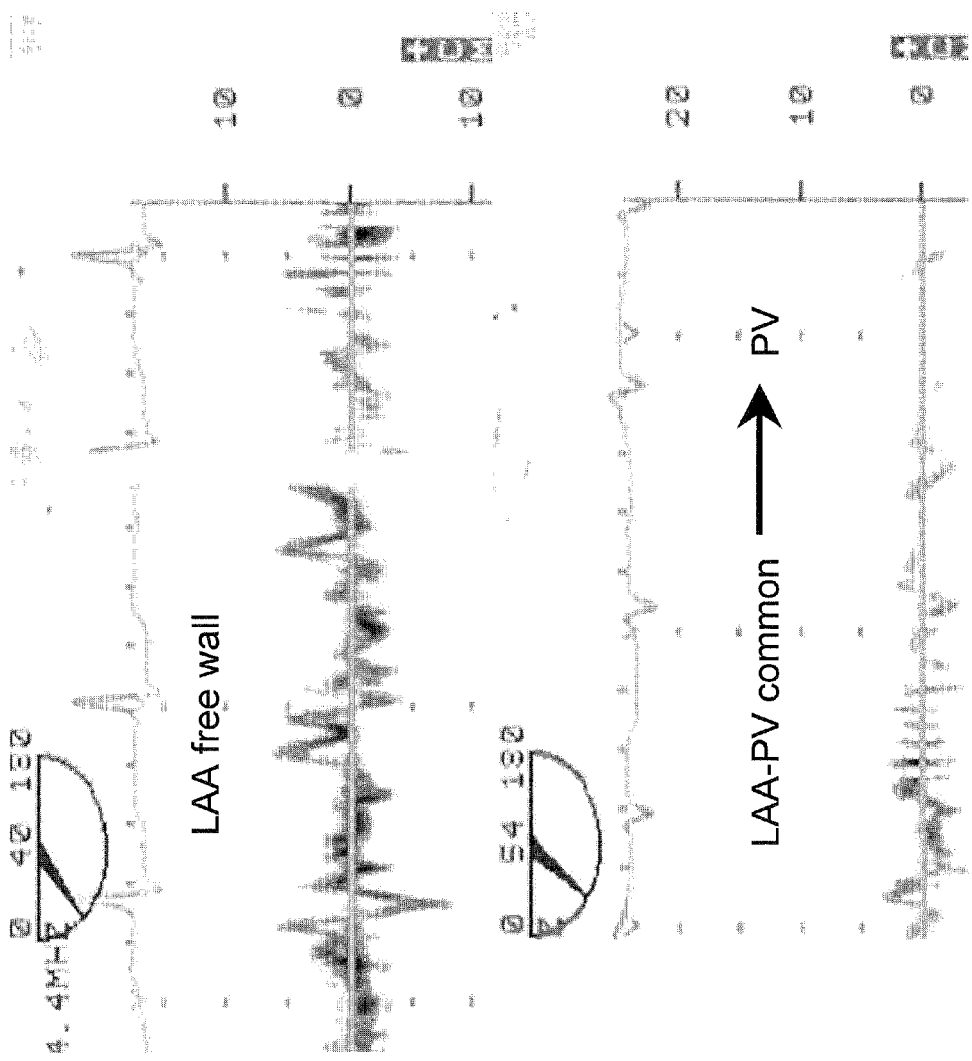
FIG. 9 is ultrasonic pulsed wave Doppler signals detected as the catheter moves from a fibrillating appendage toward the pulmonary vein and illustrates how the level ramps from the effect's magnitude to a fade level over a fade time corresponding to the intra-cardiac movement imposed onto the catheter's distal portion at varying locations.

In order to better understand the importance of PO/PC, consider the region between the pulmonary veins and left atrial appendage during atrial fibrillation (FIG. 9). The characteristic motion (e.g. frequency and displacement information) is both highly dissipative and active in juxtaposed regions. The active region requires a PC to add damping as to maintain stability. If the sensor is opposed to dissipative tissue a large accumulation of positive energy in the PO is built up. Upon switching to the active region (LAA), the PO may not act until the net energy becomes negative, causing a delay while the accumulated excess of passivity is reduced. During that delay, the system can exhibit unstable behavior. Having a PO that tracks a reference energy system (e.g. 3D catheter navigational system) minimizes the problem of resetting (Otaduy M A. Haptic Rendering; Foundations, Algorithms and Applications. A.K. Peters Ltd. 2008. 138-145). As mentioned above, adjustments in damping and passivity can be made dependent on anatomic location and physiologic data.

Other techniques or controllers for tracking and dissipating energy leaks are within the scope and spirit of the invention. For example, a port-Hamiltonian method for estimating sampled-data system errors can determine inaccuracies caused by the use of discrete-time approximations of a continuous system (Stramigioli et al. A novel theory for sample data systems passivity. IEEE/RSJ International Conference on Intelligent Robots and Systems, pp 1936-1941. Washington, D.C.: IEEE Computer Society, 2002).

Haptic Rendering

Extending Z-Width with Damping

Physical damping in the haptic control system is of paramount importance to counteract the energy generated from errors introduced by limitations in operator control, sensing and discrete-time control. Maximizing sensor resolution through use of nanosensors and minimization of sampling rate can improve performance. Physical damping mechanisms described herein and elsewhere will increase the limits of virtual stiffness and virtual damping that can be passively achieved (Otaduy M A. Haptic Rendering; Foundations, Algorithms and Applications. A.K. Peters Ltd. 2008, 127-128). Viscous damping using virtual damping techniques in the discrete-time controller can be helpful as long as it does not mask the physical damping in the system. Signal processing methods will complement mechanisms of physical damping.

Both mechanical and electrical methods of implementing high-frequency damping serve to extend Z-width. The amount of damping required is dependent upon the frequency. More damping is needed at low frequencies. At high frequencies negative virtual damping occurs due to the phase delay of the backwards difference differentiator used to compute velocity (Otaduy M A. Haptic Rendering; Foundations, Algorithms and Applications. A.K. Peters Ltd. 2008. 145-147). Thus, high order velocity filters are a hindrance to obtaining optimal passivity. For example, combining "highpass" damping and velocity filtering enables a much higher impedance virtual wall to be implemented passively.

The addition of a damper to the haptic interface will increase the maximum passive impedance. A mechanical viscous damper as described by Colgate and Brown is one example (Colgate J E, Brown J M. Factors Affecting the Z width of a Haptic Display. IEEE International Conference on Robotics and Automation. Pp 3206-3210. Washington D.C.: IEEE Computer Society, 1994). Again a limitation exists as the maximum passive virtual stiffness and damping are limited by the physical dissipation in the mechanism. This additional physical damping can be counteracted using digital control and the addition of a low-passed version of generated force to the measured damper force. In a preferred embodiment, multiple force sensors positioned about the inserted medical instrument help analyze these forces. By this method, we can mask the user's perception of damping at the low frequencies of human voluntary motion while improving the system stability and passivity at high frequencies where discrete-time control is ineffectual and energy leaks are most problematic. One method for accomplishing this is by designing analog force sensors by motor controllers that locally monitor multiple nodes/joints along introduced catheter/sheath/lead system where catheter deflection is controlled. This would be most important at the distal aspect of an ablation catheter for fine motor control of locations where ablative energies are delivered. Coupling stiffness and damping can be thus be controlled with multiple analog motor controllers (Kawai M, and Yoshikawa T, Haptic Display of Movable Virtual Object with Inerface Device Capable of Continuous-Time Impedance Display by Analog Circuit. In IEEE International Conference on Robotics and Automation, pp. 229-234. Washington, D.C.: IEEE Computer Society 2002). Use of extrinsic systems (e.g. three-dimensional navigational technologies) to determine motion characteristics and forces along multiple sites along an inserted catheter/instrument is within the scope and spirit of the invention and in one embodiment, replaces the need for multiple intrinsic (i.e. intravascular/intra-cardiac) sensors.

Haptic Rendering

Physical and Electrical Damping

A variety of dampers may be used as described in the inventor's co-pending patent applications. By way of example, typical physical dampers, magnetic dampers using eddy currents, magneticorheological dampers and mechanical brakes can be implemented and incorporated into the DSP and/or haptic handle. The damper implemented should have the fastest dynamic response. Analog methods for rendering continuous time behavior can be implemented in place of or in conjunction with mechanical dampers. A controller using a resistor and capacitor in parallel with an electric motor adds frequency-dependent electrical damping. Electric motors are gyrators and a damper on the mechanical side of the motor acts as a resistor on the electrical side of the motor. Alternate means for effectively damping the haptic system at varying frequencies are within the scope and spirit of the invention. These include but are not limited to electrical and physical methodologies.

Numerous modifications may be made to this invention without departing from its scope as defined in the appended claims.

The invention claimed is:
1. A method of simulating dynamic characteristics of moving biological tissue of a patient using tactile sensations in a haptic handle adapted to be held in the hand of a user, having one or more tactile elements and one or more corresponding actuators, comprising:
providing a plurality of sensors adapted to acquire data from moving biological tissue of the patient;
using the acquired data to generate sensor signals indicative of dynamic characteristics of sensed biological tissue that occur over a plurality of cardiac cycles of the patient;
using a processor to receive and convert sensor signals to tactile signals; and
receiving tactile signals in the haptic handle, and in response to the tactile signals, causing the one or more tactile elements to provide a tactile rendering of a time-varying representation of the dynamic characteristics to a user via the haptic handle.

2. The method of claim 1, wherein the haptic handle enables local, remote or teleoperated control of a diagnostic or treatment system that provides haptic feedback representative of the dynamic characteristics of sensed biological tissue.

3. The method of claim 2, wherein the diagnostic or treatment system utilizes at least one of the following: an externally located positioning system; ultrasound; electromagnetic energy; radiographic imaging; magnetic energy; impedance; electrical resistance; electrical energy; acoustic energy; and thermal energy.

4. The method of claim 1, wherein the one or more actuators contained within the haptic handle are capable of displacement in three dimensions according to sensor signals generated to provide multidimensional tactile sensations to the user that are characteristic of one or more of the following cardiac tissue motion and blood flow properties: pressure, force, turbulence, and laminarity.

5. The method of claim 1, wherein a haptic portion of the haptic handle is operably configured to attach and detach to an elongated element.

6. The method of claim 5, wherein the elongated element includes at least one of the following types of probes: intra-cardiac, extra-cardiac, intra-vascular, invasive, and non-invasive.

7. The method of claim 1, wherein a haptic portion of the haptic handle is contained within a conventional handle.

8. The method of claim 7, wherein the conventional handle includes at least one of the following types of probes: intra-cardiac, extra-cardiac, intra-vascular, invasive, and non-invasive.

9. The method of claim 1, wherein the acquired data relates to a rendering of properties of at least one of the following: a moving biological tissue where said tissue is largely a solid or fluid medium, a boundary between moving biological fluid and solid tissue, a biological solid tissue or fluid impacted by an inserted instrument.

10. The method of claim 9, wherein the moving biological solid tissue or fluid of the patient includes at least one of the following: left atrial appendage, pulmonary vein, interatrial septum, myocardium, and blood.

11. The method of claim 1, wherein the haptic handle is operably configured to be attachable and detachable to a probe that transmits at least of the following types of energy: ultrasound; electromagnetic; magnetic; electrical; and thermal.

12. The method of claim 1, wherein the haptic handle further provides a tactile rendering representative of registration of tissue boundaries and instantaneous haptic feedback of catheter to tissue contact to enable the user to improve intra-cardiac anatomy identification in real-time and react to cyclical variations in contact force due to cardiac contraction, torsion, translation, relaxation, and respiration.

13. The method of claim 1, wherein the tactile signals have intensities and characteristics that are controlled by the processor according to the anatomic location of one or more intra-cardiac, intra-vascular, or external sensors.

14. The method of claim 3, wherein the diagnostic or treatment system utilizes at least one of the following: an externally located positioning system; ultrasound; electromagnetic energy; radiographic imaging; magnetic energy; impedance; electrical resistance; electrical energy; acoustic energy; and thermal energy; for data acquisition of properties related to at least one of the following; a moving biological tissue where said tissue is largely a solid or fluid medium, a boundary between moving biological fluid and solid tissue, a biological solid tissue or fluid impacted by an inserted instrument.

* * * * *